United States Patent
Bardy et al.

(10) Patent No.: US 12,168,138 B2
(45) Date of Patent: Dec. 17, 2024

(54) EXTERNAL DEFIBRILLATOR

(71) Applicant: Bardy Technologies, Inc., Vashon, WA (US)

(72) Inventors: Gust H. Bardy, Carnation, WA (US); Jason Felix, Vashon Island, WA (US); Joshua Djon Green, Seattle, WA (US)

(73) Assignee: Bardy Technologies, Inc., Vashon, WA (US)

( * ) Notice: Subject to any disclaimer, the term of this patent is extended or adjusted under 35 U.S.C. 154(b) by 0 days.

(21) Appl. No.: 18/483,514

(22) Filed: Oct. 9, 2023

(65) Prior Publication Data
US 2024/0238606 A1    Jul. 18, 2024

Related U.S. Application Data

(63) Continuation of application No. 18/156,318, filed on Jan. 18, 2023, now Pat. No. 11,794,026.

(51) Int. Cl.
*A61N 1/39*    (2006.01)
*A61N 1/04*    (2006.01)

(52) U.S. Cl.
CPC ......... *A61N 1/3912* (2013.01); *A61N 1/3937* (2013.01); *A61N 1/046* (2013.01)

(58) Field of Classification Search
CPC ..... A61N 1/3912; A61N 1/3937; A61N 1/046
See application file for complete search history.

(56) References Cited

U.S. PATENT DOCUMENTS

| | | | |
|---|---|---|---|
| 5,957,956 A * | 9/1999 | Kroll | A61N 1/375 607/5 |
| 6,662,056 B2 | 12/2003 | Picardo et al. | |
| 7,072,712 B2 | 7/2006 | Kroll et al. | |
| 7,495,413 B2 | 2/2009 | Vaiosnys et al. | |
| 9,168,386 B2 | 10/2015 | Schwibner et al. | |
| 9,889,311 B2 | 2/2018 | Horseman | |
| 10,093,675 B2 | 10/2018 | Zahajska et al. | |
| 10,449,380 B2 | 10/2019 | Andrews et al. | |
| 10,543,376 B2 | 1/2020 | Beyer et al. | |
| 10,668,296 B2 | 6/2020 | Meir | |
| 10,773,091 B2 | 9/2020 | Andrews et al. | |
| 10,799,709 B2 | 10/2020 | Teber | |

(Continued)

OTHER PUBLICATIONS

A.Capucci et al. "Community-based automated external defibrillator only resuscitation for out-of-hospital cardiac arrest patients," American Heart Journal, vol. 172, 2016, pp. 192-200, https://doi.org/10.1016/j.ahj.2015.10.018.

(Continued)

*Primary Examiner* — Eric D. Bertram
(74) *Attorney, Agent, or Firm* — Krista A. Wittman

(57) ABSTRACT

An external defibrillator for use in generating a defibrillation waveform is described. The external defibrillator includes a low voltage energy storage module having one or more low voltage ultra-capacitors that store low voltage energy. A pulse transformer converts the low voltage energy to high voltage defibrillation energy and provides the defibrillation energy to a pair of electrodes configured to be applied to a patient. A modulator receives the low voltage energy from the low voltage energy storage module and transfers the low voltage energy to the pulse transformer. The external defibrillator also includes a battery.

20 Claims, 11 Drawing Sheets

(56) References Cited

U.S. PATENT DOCUMENTS

| | | | |
|---|---|---|---|
| 11,077,311 | B2 | 8/2021 | Beyer et al. |
| 11,097,121 | B2 | 8/2021 | Beyer et al. |
| 11,213,454 | B1 | 1/2022 | Shaker et al. |
| 11,305,128 | B1 | 4/2022 | Beyer et al. |
| 11,318,322 | B2 | 5/2022 | Beyer et al. |
| 11,547,863 | B1* | 1/2023 | Shaker ............... A61N 1/3904 |
| 11,794,026 | B1* | 10/2023 | Bardy ................ A61N 1/3981 |
| 2003/0080712 | A1* | 5/2003 | Tamura ............... A61N 1/3975 320/103 |
| 2004/0044371 | A1 | 3/2004 | Tamura et al. |
| 2004/0143297 | A1 | 7/2004 | Ramsey, III |
| 2005/0021094 | A1 | 1/2005 | Ostroff et al. |
| 2006/0178865 | A1 | 8/2006 | Edwards et al. |
| 2009/0256527 | A1 | 10/2009 | Welsch et al. |
| 2011/0046688 | A1 | 2/2011 | Schwibner et al. |
| 2011/0202101 | A1* | 8/2011 | Tan ..................... G09B 19/003 607/7 |
| 2014/0317914 | A1 | 10/2014 | Shaker et al. |
| 2014/0324111 | A1* | 10/2014 | Wu ..................... A61N 1/3968 607/7 |
| 2017/0157415 | A1 | 6/2017 | Horseman |
| 2018/0140859 | A1 | 5/2018 | Meir |
| 2018/0280708 | A1* | 10/2018 | Escalona ............. H02J 50/10 |
| 2018/0318592 | A1 | 11/2018 | Smith |
| 2019/0044362 | A1* | 2/2019 | Beyer ................. H02J 7/00714 |
| 2019/0117989 | A1 | 4/2019 | Andrews et al. |
| 2019/0356492 | A1* | 11/2019 | Picco ................. H04L 67/125 |
| 2021/0093877 | A1* | 4/2021 | Beyer ............... H02J 7/007182 |
| 2023/0041857 | A1* | 2/2023 | Prutchi ................ A61N 1/378 |
| 2023/0089192 | A1* | 3/2023 | Bennett ............... A61N 1/046 607/142 |

OTHER PUBLICATIONS

J. W. Gundry et al. "Comparison of Naive Sixth-Grade Children With Trained Professionals in the Use of an Automated External Defibrillator," Circulation Oct. 19, 1999; Downloaded from http://ahajournals.org by on Oct. 22, 2022.

D. Aschieri et al. "Ventricular Fibrillation Recurrences in Successfully Shocked Out-of-Hospital Cardiac Arrests," Medicina 2021, 57, 358. https://doi.org/10.3390/medicina57040358.

G. H. Bardy et al. "A Prospective Randomized Evaluation of Biphasic Versus Monophasic Waveform Pulses on Defibrillation Efficacy in Humans," Cardiac Pacing, Biphasic Versus Monophasic Defibrillation, JACC vol. 14, No. Sep. 3, 1989:728-733.

G. H. Bardy et al. "A Prospective Randomized Comparison in Humans of Biphasic Waveform 60-μF and 120-μF Capacitance Pulses Using A Unipolar Defibrillation System," Originally published Jan. 1, 1995 https://doi.org/10.1161/01.CIR.91.1.91 Circulation. 1995;91:91-95.

HeartSine® samaritan® PAD 350P/360P AEDs Semi-automatic/fully automatic public access defibrillators, "Compact, easy-to-use, lifesaving technology for public access" H009-032-340-AE_350P_360P_Data_ENUS_0521_web-3.

HeartSine® samaritan® PAD 350P/360P Connected AEDs Semi-automatic/fully automatic public access defibrillators with integrated Wi-Fi® connectivity; "Readiness matters," H009-043-010-AD_Connected_350P_360P_Data_ENUS_0521_web.

"Defibtech Lifeline ECG Semi-Automatic Defibrillator with ECG Display Technical Specifications†," DAC-A2702EN-BC Issued: Jan. 15, 2021. Defibtech, LLC • Guilford, CT 06437 USA • 1-203-453-4507 • 1-866-DEFIB-4U (1-866-333-4248) www.defibtech.com.

\* cited by examiner

130

190

EXTERNAL DEFIBRILLATOR

CROSS-REFERENCE TO RELATED APPLICATION

This non-provisional patent application is a continuation of U.S. Pat. No. 11,794,026, issued Oct. 24, 2023, the priority date of which is claimed and the disclosure of which is incorporated by reference.

FIELD

This invention relates in general, to circuits for generating defibrillation waveforms and in particular, to an external defibrillator.

BACKGROUND

Sudden cardiac arrest (SCA) is a significant cause of mortality throughout the world and remains a major public health concern causing about 300,000 to 450,000 deaths each year in the United States alone, despite the broad scale teaching of cardiopulmonary resuscitation (CPR) and the implementation of public access automated external defibrillators (AED) in hospitals, ambulances and other public locations, like airports and stadiums. More than 9 of 10 SCA victims die, even in locales with advanced medic response systems. In most locations, the death rate approaches 100%.

SCA occurs when the heart suddenly and unexpectedly stops pumping blood, most commonly caused by a chaotic cardiac rhythm disorder known as ventricular fibrillation (VF). VF is a lethal heart rhythm abnormality that causes the ventricles of the heart to quiver ineffectively, resulting in a failure to pump blood. Accordingly, blood pressure plummets and blood delivery to the brain and all bodily organs essential ceases in 5-10 seconds.

SCA from VF constitutes the most time-critical emergency in medicine and is universally lethal within 10-20 minutes without prompt medical attention, specifically the delivery of a high-voltage, high-energy shock across the chest via a defibrillator, the only method known to stop VF. Preferably such a shock is delivered within 5 minutes of the onset of VF.

Victims of VF collapse within 5-10 seconds, lose consciousness, and become unresponsive. Only someone that is physically near the victim has a meaningful chance at preventing death. The chance of survival rapidly decreases 7-10% per minute from onset of VF and, after 10 minutes, resuscitation rarely succeeds, even with CPR, and even if an AED is used, as the heart and brain will have suffered irreversible injuries.

Consequently, ensuring that people have immediate access to an AED is absolutely essential to saving lives from cardiac arrest, where every minute counts.

AEDs made publicly available, however, have not meaningfully addressed the problem of SCA. By various accounts, there are approximately 3.2 to 4.5 million AEDs currently deployed in public places in the United States, yet an estimated more than 30 million AEDs are needed to provide sufficient coverage to meaningfully improve cardiac arrest survival rate nationally. Moreover, despite this disparity between the number of devices versus the estimated need, increasing the number of public access AEDs by an order of magnitude would be neither practical in terms of cost or execution nor would such an increase address the problem that SCAs primarily occur in places other than where public access AEDs are found. More than 70% of VF cases occur in or near the home or during routine activities of daily living, like yard-work and gardening, driving, personal recreation, and so on, locations where public access AEDs are not usually found. Although immediate employment of an AED from time of victim collapse to shock delivery is optimal for survival, public access AEDs are rarely deployed or used in locations where SCAs typically happen and, if they are, their use often comes far too late. Thus, the problem of resuscitating victims from VF is inexorably linked to time and proximity to an AED, which are, in turn, inexorably linked to convenience of use, which is a direct consequence of AED cost, size and weight. Accordingly, to make a positive impact of survivability requires a different approach to AED deployment. One solution would be to provide AED devices that are pocket-sized and modest in weight and cost, so that AEDs become practically ubiquitous, similar to a mobile phone.

The high cost and bulk of conventional public access AEDs are mainly due to the design choices of reusability, elimination of all possible failure modes, and telemetry functionality intended to constantly perform and transmit multi-use readiness checks. Typical AEDs perform self-testing constantly, which depletes the battery, and causes wear on the critical components, requiring large and complex circuit designs and components that will survive constant testing and the resulting high voltage bias that is induced. Several AED product recalls have shown this practice to prematurely degrade components, resulting in an AED becoming non-functional when needed. AEDs are typically designed to eliminate failure modes, which, paradoxically, results in large and complex custom components that are expensive and prone to failure. For example, conventional public access AED capacitors are often rated for 90° C. and 20,000 discharges back-to-back, conditions that do not remotely resemble the typical use case under any conceivable scenario. Moreover, reusability requirements mean that the batteries must be able to store enough energy to defibrillate multiple patients, perform simulated use testing, as well as have a circuit able to sense when there is not enough energy to be "rescue ready" far in the future.

These are key factors that effectively restrict deployment of public access AEDs to healthcare providers, first responders, and public areas that are legally required to have an AED, all of which make existing AEDs relatively unavailable and of no use for the majority of VF emergencies that occur at or near the home away from public access AEDs. Moreover, public access AEDs are packaged in large carrying cases weighing several pounds that are too bulky to be convenient for ubiquitous use by the public. Furthermore, AEDs typically cost between $1000 to $2200, which is too expensive for the average person to buy or to serve as an accessory to accompany activities of daily living.

Therefore, a need remains for providing a new circuit design for rapidly generating high voltage therapeutic defibrillation waveforms that in turn facilitates the design of low cost and convenient pocket-sized AEDs. Such a design will also decrease the cost and bulk of conventional AEDs and defibrillation circuits in general, be they external or internal defibrillators.

SUMMARY

A low voltage energy storage circuit is described that can be either supplementary to or in lieu of a traditional circuit for generating high energy defibrillation waveforms for use in an external defibrillator. Use of this circuit can decrease the cost, size and weight of AEDs and, more broadly, on the design of a defibrillation circuit as used in any form of external defibrillator. For instance, the high-voltage pulse capacitor used to store the defibrillation energy in conventional AED circuit designs can be substantially decreased in energy storage, voltage rating and capacitance, resulting in higher reliability, smaller size, smaller weight and decreased cost. This low voltage energy storage circuit can be used to create a low cost and high convenience AED in a small form factor, for instance, about the size and weight of a mobile telephone and suitable to fit in a shirt pocket, hip pocket, or small purse. This circuit also can be used to augment or replace any high voltage charging and energy storage circuits found in conventional external defibrillation circuit designs, including the charging circuits used in AEDs and hospital-based defibrillators, and further, can be adapted for use in future implantable defibrillators.

One embodiment provides a circuit with low voltage energy storage for use in generating defibrillation waveforms. A charging circuit includes a pulse capacitor that stores defibrillation energy. The charging circuit also includes a high voltage generator circuit that includes an inductor (used in a boost configuration) or transformer, including a flyback, step-up or pulse transformer, and a rectification circuit through which the pulse capacitor is charged with the defibrillation energy. The charging circuit also includes a discharge and polarity control circuit electrically connected to the pulse capacitor as inputs and switchable to receive the defibrillation energy, which is output as a defibrillation waveform. A low voltage energy supplementing circuit is electrically connected to the pulse capacitor in line with the high voltage generator circuit and stores supplemental defibrillation energy. A microcontroller is adapted to enable the low voltage energy supplementing circuit to modulate the delivery of the stored supplemental defibrillation energy to the pulse capacitor, which can be performed in a metered or load dump fashion from the high energy density capacitors, to augment the defibrillation energy derived from the initial defibrillation waveform.

A further embodiment provides a circuit for providing a defibrillation waveform. A sensing circuit is adapted to sense a shockable cardiac rhythm that constitutes a cardiac arrest condition in a patient and, in response, generates a shock signal. A charging circuit includes a pulse capacitor that stores defibrillation energy. The charging circuit also includes a high voltage generator circuit that includes a transformer, including a flyback, step-up or pulse transformer, and a rectification circuit through which the pulse capacitor is charged with the defibrillation energy. The charging circuit also includes a discharge and polarity control circuit electrically connected to the pulse capacitor as inputs and switchable to receive the defibrillation energy, which is output as a defibrillation waveform in response to the shock signal. A low voltage energy supplementing circuit is electrically connected to the pulse capacitor in line with the high voltage generator circuit and includes one or more low voltage ultra-capacitors that store supplemental defibrillation energy. A microcontroller is adapted to enable the low voltage energy supplementing circuit to modulate the delivery of the stored supplemental defibrillation energy from the one or more low voltage ultra-capacitors to the pulse capacitor, which can be performed in a metered or load dump fashion from the high energy density capacitors, to augment the defibrillation energy derived from the initial defibrillation waveform.

A still further embodiment provides an external defibrillator with a housing, within which is contained a sensing circuit, a charging circuit, a low voltage energy supplementing circuit, a microcontroller, and a battery source. The sensing circuit is adapted to sense a shockable cardiac rhythm that constitutes a cardiac arrest condition in a patient and, in response, generate a defibrillation waveform, to shock the patient. The charging circuit includes a pulse capacitor that stores defibrillation energy. The charging circuit also includes a high voltage generator circuit that includes a transformer, including a flyback, step-up or pulse transformer, and a rectification circuit through which the pulse capacitor is charged with the defibrillation energy. The charging circuit also includes a discharge and polarity control circuit electrically connected to the pulse capacitor as inputs and switchable to receive the defibrillation energy, which is output as a defibrillation waveform in response to the signal to shock the patient. A low voltage energy supplementing circuit is electrically connected to the pulse capacitor in line with the high voltage generator circuit and includes one or more low voltage ultra-capacitors that store supplemental defibrillation energy. A microcontroller is adapted to enable the low voltage energy supplementing circuit to modulate the delivery of the stored supplemental defibrillation energy from the one or more low voltage ultra-capacitors to the pulse capacitor, which can be performed in a metered or load dump fashion from the high energy density capacitors, to augment the defibrillation energy derived from initial defibrillation waveform. The battery source powers the sensing circuit, the charging circuit, the low voltage charging circuit and the microcontroller. A pair of dermal electrodes are connected to the outputs via one or more leads over which the defibrillation waveform can be applied to the patient. In the case of the use of one lead, an outer surface of the housing serves as the second electrode.

A still further embodiment provides an external defibrillator with a housing, within which is contained a sensing circuit, a charging circuit, a low voltage energy supplementing circuit, a microcontroller, and a battery source. The housing has dimensions typically in the range of 2.25 to 3.5 inches wide, 5.25 to 7 inches tall, and 0.25 to 1.0 inches deep and a weight in the range of 130 to 550 grams. The sensing circuit is adapted to sense a shockable cardiac rhythm that constitutes a cardiac arrest condition in a patient and in response generate a shock signal. The charging circuit includes a pulse capacitor that stores defibrillation energy. The charging circuit also includes a high voltage generator circuit that includes a transformer, including a flyback, step-up or pulse transformer, and a rectification circuit through which the pulse capacitor is charged with the defibrillation energy. The charging circuit also includes a discharge and polarity control circuit electrically connected to the pulse capacitor as inputs and switchable to receive the defibrillation energy, which is output as a defibrillation waveform in response to the shock signal. A low voltage energy supplementing circuit is electrically connected to the pulse capacitor in line with the high voltage generator circuit and includes one or more low voltage ultra-capacitors that store supplemental defibrillation energy. A microcontroller is adapted to enable the low voltage energy supplementing circuit to modulate the delivery of the stored supplemental defibrillation energy from the one or more low voltage ultra-capacitors to the pulse capacitor, which can be performed in a metered or load dump fashion from the high energy density capacitors, to augment the defibrillation energy derived from the initial defibrillation waveform. The waveforms can be of a preset or variably adjustable nature given the flexibility of the microcontroller modulation system.

A still further embodiment provides an external defibrillator with a housing that includes an integrated electrode formed on an outer surface of the housing. The housing contains a sensing circuit, a charging circuit, a low voltage energy supplementing circuit, a microcontroller, and a battery source. The sensing circuit is adapted to sense a shockable cardiac rhythm that constitutes a cardiac arrest condition in a patient and in response generate a shock signal. The charging circuit includes a pulse capacitor that stores defibrillation energy. The charging circuit also includes a high voltage generator circuit that includes a transformer, including a flyback, step-up or pulse transformer, and a rectification circuit through which the pulse capacitor is charged with the defibrillation energy. The charging circuit also includes a discharge and polarity control circuit electrically connected to the pulse capacitor as inputs and switchable to receive the defibrillation energy, which is output as a defibrillation waveform in response to the shock signal. A low voltage energy supplementing circuit is electrically connected to the pulse capacitor in line with the high voltage generator circuit and includes one or more low voltage ultra-capacitors that store supplemental defibrillation energy. A microcontroller is adapted to enable the low voltage energy supplementing circuit to modulate the delivery of the stored supplemental defibrillation energy from the one or more low voltage ultra-capacitors to the pulse capacitor, which can be performed in a metered or load dump fashion from the high energy density capacitors, to augment the defibrillation energy derived from the initial defibrillation waveform. A stand-alone electrode is electrically interfaced to the discharge and polarity control circuit via a lead or similar connector. The waveforms can be of a preset or variably adjustable nature given the flexibility of the microcontroller modulation system. The defibrillation waveform is delivered to the patient via the integrated electrode and the stand-alone electrode.

A yet further embodiment provides an external defibrillator that has a housing containing a sensing circuit adapted to sense a shockable cardiac rhythm that constitutes a cardiac arrest condition in a patient, a charging circuit that includes a pulse capacitor, a high voltage generator circuit, and a discharge and polarity control circuit through which the pulse capacitor is charged with defibrillation energy generated by the high voltage generator circuit. A low voltage energy supplementing circuit is connected to the pulse capacitor in line with the high voltage generator circuit. A microcontroller is adapted to enable the low voltage energy supplementing circuit to modulate delivery of supplemental energy to the pulse capacitor to augment the defibrillation energy comprising the defibrillation waveform. The charging circuit and the low voltage energy supplementing circuit are provided for single use.

A still further embodiment provides an external defibrillator for use in generating a defibrillation waveform. The external defibrillator includes a low voltage energy storage module having one or more low voltage ultra-capacitors that store low voltage energy. A pulse transformer converts the low voltage energy to high voltage defibrillation energy and provides the defibrillation energy to a pair of electrodes configured to be applied to a patient. A modulator receives the low voltage energy from the low voltage energy storage module and transfers the low voltage energy to the pulse transformer. The external defibrillator also includes a battery.

The low voltage, high current supplementary defibrillation energy storage and delivery circuit described herein allows delivery of a high voltage, high energy defibrillation waveform using a design that decreases cost and overall device size and weight relative to current public access AEDs, heretofore unavailable, by meaningfully innovating alternatives to pulse capacitor charging. The high voltage transformer that is used to inject defibrillation energy into the patient can be packaged in a flat and thin planar design, known as a Planar Laminated High Energy Pulse Transformer. This type of transformer is optimal for energy conversion efficiency and an ideal shape for a cell phone-like design. More broadly, the supplementary defibrillation energy storage and delivery circuit can be used in external defibrillators, including pocket, public, and clinical external defibrillators found in hospitals and ambulances.

If significantly reducing the numbers of deaths from SCA due to VF is to be meaningfully addressed, which has been acknowledged as a problem for over 40 years, the design of conventional AEDs must change to lower cost, size and weight, so that AEDs can be ubiquitously made available, including in every home and every car, as well as in many pockets and purses. Here, by employing a low voltage, high current supplementary defibrillation energy storage and supplemental conversion-based delivery circuit, the acquisition and maintenance costs associated with public access AED using the high voltage, low density energy storage defibrillation circuit needed to accommodate unnecessary repetitive capabilities can be significantly lowered through reduction in battery and high-voltage pulse capacitor ratings. In turn, lower cost, size and weight will result in increased AED availability and convenience, and therefore an increased survival rate from cardiac arrest.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
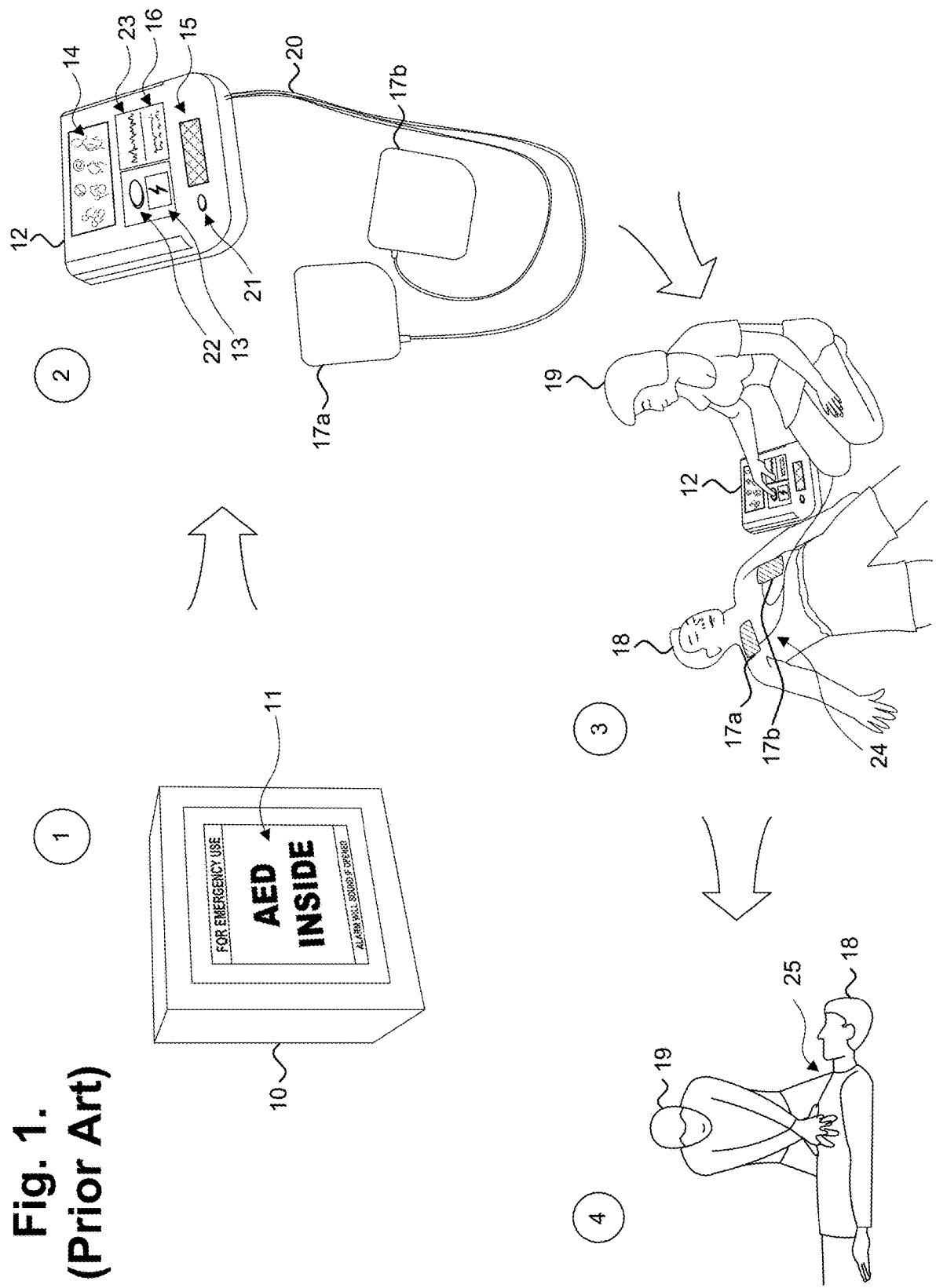
FIG. 1 is a process flow diagram showing, by way of example, a typical prior art use of a public access AED in an SCA situation.

There has been a push to deploy public access AEDs in busy often-frequented places, such as airports, restaurants, casinos, shopping centers, and stadiums. Public access AEDs are simple, easy-to-operate devices that automatically diagnose whether a shockable rhythm is present and, if so, urge delivery of defibrillation shocks by a bystander in an attempt to restore normal cardiac rhythm. FIG. 1 is a process flow diagram showing, by way of example, a typical prior art use of a public access AED 12 in an SCA situation. Public access AEDs are designed for repeated use by the general public and require minimal training to operate; users simply follow some combination of voice prompts, text prompts, or both, and diagrammatic instructions to deliver the defibrillation waveforms to SCA victims.

In this example, a victim 18 has suffered suspected cardiac arrest while in the company of a rescuer 19. The terms "victim" and "patient" are used interchangeably and refer to the individual that is receiving emergency care for a possible cardiac arrest. Similarly, the terms "rescuer," "bystander" and "user" are used interchangeably and refer to the individual who is actively providing the emergency care through the use of a public access AED.

When SCA is suspected, often when a victim suddenly loses consciousness and collapses, a rescuer 19 must take immediate action to assist the victim 18. After ideally first calling 9-1-1, the rescuer 19 should check the victim 18 for a pulse and, if absent, begin basic life support maneuvers (BLS), which begins by first locating and obtaining a public use AED 12 (step (1)). Note that there are two main categories of AEDs, either of which may be found in use as a public use AED. Some AEDs automatically deliver shocks without rescuer action when VF is detected. Most AEDs are semi-automatic and require the rescuer to manually trigger a shock with a button or device control. The portable AEDs carried by emergency medical services (EMS) personnel are generally designed as semi-automatic AEDs that include physiological monitoring tools for both basic and advanced life support, as well as include advanced CPR feedback and vital signs patient monitoring.

A typical public access AED 12 is located where the general public ordinarily has access kept in some type of protective housing 10, such as a display case, wall cabinet or kiosk. Public access AEDs are designed for long-term reuse and to be available to save multiple victims over their service lifetime. Thus, these devices are physically robust to withstand rough and repeated use, complicating factors that add to unit cost and size, including maintenance obligations and telemetry functionality needed to prevent failures and sustain readiness over time. The public access AED 12 itself is portable and therefore susceptible to being misplaced or stolen; the protective housing 11 helps to keep the public access AED 12 secure and available until needed. Note that, despite being portable, a public access AED kit is bulky and weighs several pounds, which makes carrying a public access-type AED on an everyday basis impractical for most people, even though wider AED availability and use could help save more lives. In addition, both the electrodes and batteries of public access AEDs have expiration dates and must be replaced upon their respective expiry every one to three years. Moreover, these AEDs must undergo periodic operational testing that may require that the defibrillation circuit be energized, resulting in a depleted battery charge and prematurely degrading the circuit.

Returning to the steps of AED use in public, once the rescuer 19 locates and obtains an AED, the rescuer must activate the AED 12, which generally entails pressing an "On" button or other simple-to-use control (step (2)). Conventional public use AEDs 12 are packaged in a large carrying case that contains the AED circuit, including sensing and defibrillation circuit and battery, a pair of shock paddles (not shown) or, more commonly, adhesive dermal electrode pads 17a-b connected by a set of leads 20, and support accessories (not shown), such as gloves and a face shield. Note that shock paddles and adhesive electrode pads are both acceptable modes for delivering defibrillation shocks and when used correctly, are equally efficacious. Conventional shock paddles and electrode pads are generally about 8-12 cm in length, rectangular, and intended to conform to the human thoracic anatomy.

As most rescuers will be lay bystanders, public use AEDs generally provide visual instructions 14 on assessing the victim's breathing and placement of its electrode pads 17a-b on the victim's chest 24 (step (3)). The AED includes a set of necessarily simple controls, typically an "On" button 21 and, if the AED is semi-automatic, a "Shock" button 22 to manually deliver a defibrillation shock by the rescuer, plus a warning indicator 13 that the AED is charged and ready to deliver a defibrillation shock. To activate the public use AED 12, the rescuer 19 simply presses the "On" button 21. The visual instructions 14 are typically supplemented with speaker-generated voice prompts 15, display-generated text prompts 16, in some cases, an electrocardiogram (ECG) 23, or some combination of voice prompts, text prompts and an ECG. The American Heart Association (AHA) and European Resuscitation Counsel (ERC) publishes guidelines outlining a recommended sequence of visual and voice prompts to help rescuers in proper use of AEDs. See, 2010 *American Heart Association Guidelines for CPR and ECC; Supplement to Circulation*, Vol. 192, Issue 18 (Nov. 12, 2010). *European Resuscitation Council Guidelines for Resuscitation* 2010, *Resuscitation* Volume 81 (October 2010).

The paddles or electrode pads 17*a-b* must be applied by the rescuer 19 to be in direct contact with the victim's skin. Electrode pads are typically adhesive and, in many AED kits, a razor is included to shave any hair off the victim's skin, if needed, on the anatomy where electrode pads are to be placed. To maximize the transit of current through the heart, an anterior-lateral position for paddle or electrode pad placement on the victim's chest 24 is preferred. The anterior paddle or pad is applied on the right anterior chest 24 just below the right clavicle. The lateral paddle or pad is applied immediately below and lateral to the left nipple. In female patients, the lateral paddle or pad should be applied on the chest wall below and lateral to the left breast, and not over the breast tissue. Alternative acceptable paddle or pad positions include the anterior-posterior and apex-posterior orientations.

With the paddles or pads in place, the AED will determine if a shockable rhythm is present depending upon the ECG obtained from the paddles or pads and instruct the rescuer to deliver a defibrillation shock, if required, to stop the arrhythmia and allow the heart to reestablish an effective normal rhythm. If the public use AED 12 is semi-automatic, the rescuer 19 will need to manually administer the shock by pressing the "Shock" button 22. Conventionally, every shock cycle includes one to two minutes of CPR chest compressions 25 by the rescuer 19 followed by rhythm analysis by the AED (step (4)); as many as three defibrillation shocks may be required, after which resuscitation of the victim 18 is unlikely. Alternatively, depending on outcome of the initial shock, repetitive sequenced shocks may be delivered. CPR may or may not be required after a successful defibrillation or between rapidly delivered, serial shocks. Some AEDs provide for escalating energy delivery when a previous shock attempt fails to terminate VF as determined by the ECG. Higher energy delivery is more likely to restart the heart, but also more likely to cause temporary damage to cardiac tissue. Higher shock energies also result in increased weight and cost of the AED and usually not required early in the rescue process.

Public access AEDs are designed and built to save multiple victims over the service life of the device despite long periods of idle standby storage. These requirements lead to a complex and typically over-engineered design, which also leads to high cost and long-term maintenance obligations. The design and construction of public use AEDs is deliberately robust with large heavy batteries and costly electronic components intended to ensure operability when and if the AED is needed for use.

As public use AEDs are big and bulky, they are ordinarily only going to be found in a stationary place in a controlled access protective housing, which inherently limits their availability during a SCA emergency and, to a large extent, renders public use AEDs largely ineffective in reducing the number of deaths caused by most SCA deaths that occur in private settings. Public use-type AEDs are also expensive and seldom found outside of areas where their placement is legally required given the significant economic burden associated with both initial acquisition and ongoing maintenance costs that often exceed the initial price of the AED. Thus, even though most SCAs occur in the home, AEDs are seldom found there, or in countless other random places where people often suffer a SCA, such as in cars and private boats, in parks or trails where people are walking, exercising or enjoying the outdoors, and where people are visiting with friends, and so forth. Despite being portable, the size and weight of a full public use AED kit makes carrying one personally in a backpack or stowed in the glove box of a car impractical.

Conventional AEDs are battery powered and include a charging circuit that uses a step-up transformer to increase battery voltage from low voltage in the range of 6-24 volts (V) to around 1000-6000 V (note that higher voltages are rarely used today), a rectification circuit to convert the high voltage AC energy from the step-up transformer to direct current (DC) energy, and a pulse capacitor to store the energy prior to defibrillation shock delivery. These traditional pulse capacitors are rated to handle high voltage and large sudden discharge currents; as a result, they can be difficult to manufacture and are prone to failure, thereby increasing associated costs. Once this type of legacy pulse capacitor is charged, the AED is ready to deliver a defibrillation shock and the charging circuit switches the energy to the patient, whereby the current is delivered to the victim's chest to complete the circuit. For successful defibrillation, the current delivery waveform must be physiologically appropriate.

Current commercially available AEDs generally employ biphasic truncated exponential (BTE), pulsed biphasic, or rectilinear biphasic waveforms. In contrast to the historical use of monophasic waveforms, biphasic waveforms are both more effective and require less energy for defibrillation. Consequently, patient outcome is statistically better over time. Accordingly, monophasic waveforms are no longer used. With a biphasic defibrillator, the initial energy level for defibrillation typically begins at 120 J (although it can be less) and can escalate for the second and subsequent defibrillation shocks up to a maximum of 360 J. Energy choice and escalation are waveform- and manufacturer-specific.

The life-saving benefits of AEDs can be efficaciously provided to every person, everywhere and on a 24/7/365 basis through a disposable, single-use AED that is small enough to be truly portable, for instance by fitting in an average-sized pocket. A single use AED, that is, a device that is available to therapeutically treat one instance of SCA, significantly streamlines and simplifies the design requirements of the AED and accordingly makes it possible to house the AED in a small pocketable form factor. Periodic maintenance is not required, as the disposable nature of the pocket AED implies the device will be discarded before needing to undergo maintenance or other testing prior to use on a patient. As well, the failure ratings of the electronic components need only accommodate one use, rather than repeated uses over an extended service life of many years, limiting complexity and improving durability. Similarly, the battery can be smaller and lighter, as battery life will not be depleted by long shelf life and telemetry transmissions related to diagnostic routines and maintenance cycles. Further, the use of such simplified electronic components and battery technologies lowers cost and allows disposability to be realized. Finally, to encourage being carried by users at all times, the pocket AED is sized comparably to a conventional smartphone, for instance, in the range of 2.25 to 3.5 inches wide, 5.25 to 7 inches tall, and 0.25 to 1.0 inches deep, and of similar weight, for example, in the range of 130 to 550 grams.

Figure 2:
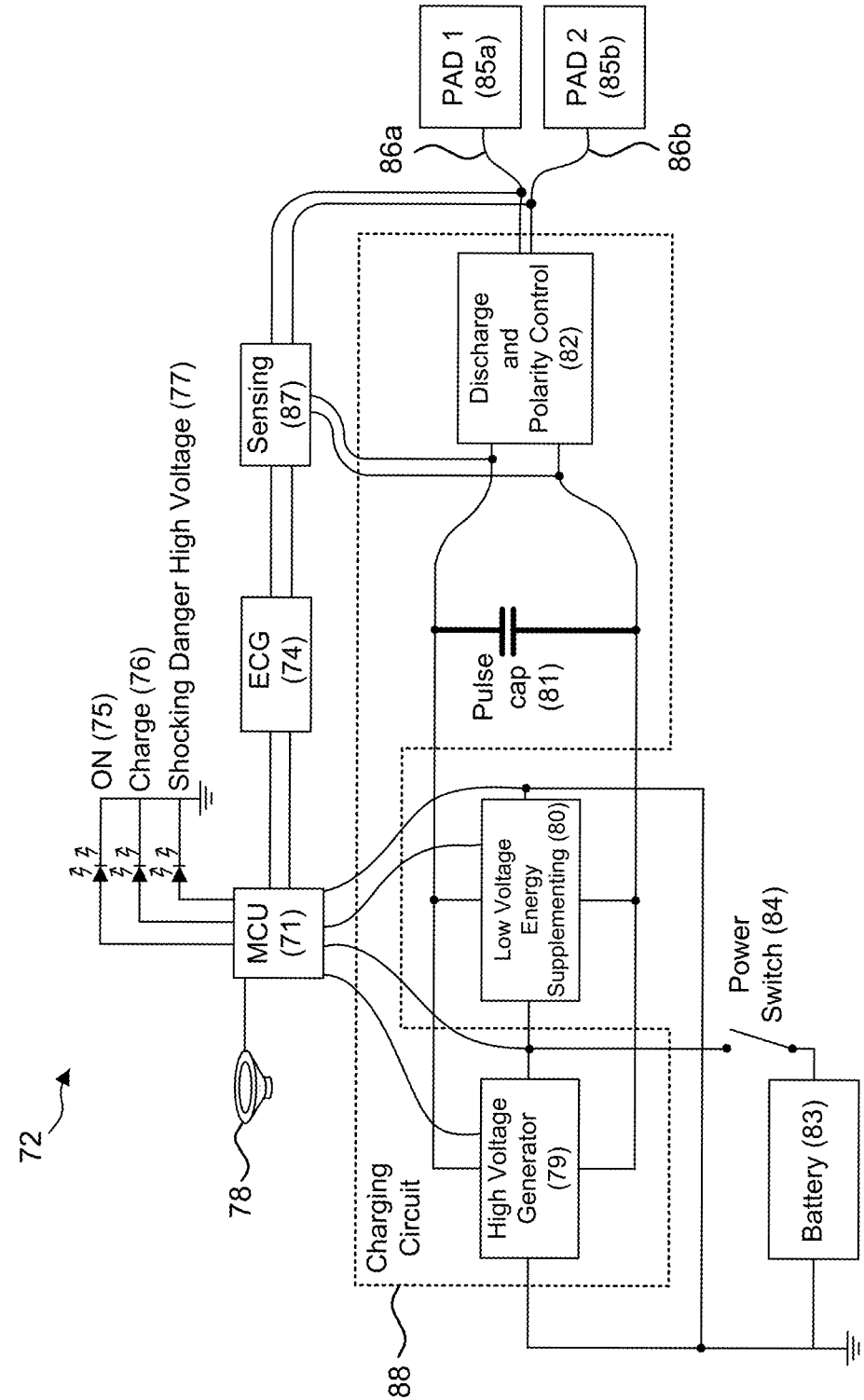
FIG. 2 is a block diagram showing functional components and a user interface for a disposable single use pocketable AED in accordance with one embodiment.

To facilitate the construction of a disposable pocketable AED to fit into a small form factor, the defibrillation circuit utilizes a therapy delivery (shock) methodology that utilizes low voltage energy storage and supplementation. FIG. 2 is a block diagram showing functional components and a user interface 72 for a disposable pocketable AED. For the sake of clarity, only the defibrillation circuit 70 will be discussed in detail.

The defibrillation circuit 70 includes components for providing a basic user interface 72 that includes an "On" switch (not shown), a "Power On Indicator" 75, a charging indicator 76, and optionally, a warning indicator 77 that indicates defibrillation shock delivery readiness with attendant dangers of exposure to high voltage, plus an optional speaker 78 through which audible instructions can be played. The user interface 72 also includes a visual display (not shown) on which text prompts can be displayed. In one embodiment, an AED incorporating the defibrillation circuit 70 can be semi-automatic and require the rescuer to manually trigger a shock by actuating the charging indicator 76; in a further embodiment, an AED incorporating the defibrillation circuit 70 employs a circuit to automatically deliver the defibrillation shock to the victim without user action once the charging circuit is ready, that is, the pulse capacitor is charged, and after the user has been warned to avoid any direct physical contact with the patient during shock delivery.

The defibrillation circuit 70 is controlled by a microcontroller unit (MCU) 71 or system-on-chip controller (SOC) (not shown) that is micro programmable, which allows updated controller firmware to be downloaded from an external programmer into a persistent memory store. Sensing circuit 87 is connected in line with the inputs and outputs of a discharge and polarity control circuit 82. The sensing circuit 87 determines whether a shockable rhythm is present and monitors for the MCU 71 the defibrillation energy that is received from the pulse capacitor 81 as an input to the discharge and polarity control circuit 82 and the defibrillation waveform or "pulse" that is output. ECG front end circuit 74 evaluates heart rhythm for the MCU 71. The ECG front end circuit 74 taps off the leads 86a-b of the pair of electrode pads 85a-b to sense cardiac signals, while the sensing circuit 87 taps off the discharge and polarity control module's input leads to monitor the shock delivery process. In a further embodiment, the MCU 71 interfaces to the sensing circuit 87 to continually measure patient impedance and adjusts parameters in the high voltage generator module 79 and the low voltage energy supplementing module 80 to alter one or more of energy, voltage and pulse width in real time, as further discussed infra with reference to FIG. 8. The sensing circuit 87 is implemented through conventional VF detection algorithms to detect the presence of a shockable rhythm, such as published by A. Fan, et al., Shockable Rhythm Detection Algorithms for Electrocardiograph Rhythm in Automated Defibrillators, AASRI Conf. on Comp. Intel. and Bioinfor. pp. 21-26 (2012). The ECG front end circuit 74 is implemented through conventional heart function evaluation algorithms, such as provided through the ADS1x9xECG-FE family of integrated analog front-end ECG circuits, available from Texas Instruments, Dallas, TX. Other types and configurations of sensing and ECG front end circuitries are possible.

When a shockable rhythm is detected, based on inputs from the sensing circuit 87 and the ECG front end circuit 74, the MCU 71 determines the parameters of a defibrillation waveform in terms of energy, voltage, and pulse width; the defibrillation waveform is algorithmically selected based on the nature of the shockable rhythm to be medically appropriate for restoring normal cardiac rhythm. Up to a maximum of three shocks may be needed if the victim fails to be resuscitated, after which further shocks are generally futile.

In response to the sensing circuit 87 determining that a shockable rhythm is still present after initial shock delivery, that is, defibrillation failed to establish normal cardiac rhythm, the MCU 71 may simply repeat the delivery of the defibrillation pulse or, if appropriate, revise the parameters of the defibrillation waveforms for the subsequent pulses. In this situation, subsequent defibrillation shocks may need to be escalated for the second and subsequent defibrillation shocks, generally up to a maximum of 360 J. In a further embodiment, parameters consisting of one or more of energy, voltage and pulse width are adjusted by the MCU 71 in real time, as further discussed infra with reference to FIG. 8.

Defibrillation energy is generated through a combination of a modified conventional charging circuit 88 and a low voltage energy supplementing module 80 which are cooperatively controlled by the MCU 71. The charging circuit 88 includes a high voltage generator module 79, which conventionally charges a high-voltage pulse capacitor 81 with energy that is stored for delivery as a defibrillation shock. The charging circuit 88 also includes a discharge and polarity control module 82, optionally in the form of an H-bridge, that switches in response to the sensing circuit 87, or, where the AED is semi-automatic, in response to the pressing of the "Shock" button or similar manual control, to deliver an appropriate defibrillation shock over the electrode pads 85a-b. Other configurations of switching elements in lieu of or in addition to an H-bridge are possible.

The discharge and polarity control module 82 interfaces over a pair of leads 86a-b to electrode pads 85a-b as outputs and to the pulse capacitor 81 as inputs. The H-bridge is formed with two "legs" on the output side containing the leads 86a-b for the electrode pads 85a-b and the other two "legs" on the input side electrically connected to a pulse capacitor 81. The discharge and polarity control module 82 is switchable to receive the defibrillation energy from the pulse capacitor 81, which is output by the discharge and polarity control module 82 as a defibrillation waveform or "pulse." In a further embodiment, the discharge and polarity control module 82 includes a polarity reversal correction circuit to ensure proper shock delivery in the event that the electrode pads 85a-b are improperly reversed. In a yet further embodiment, the polarity could automatically be reversed on the third defibrillation shock, as reversing polarity can aid in defibrillation of difficult cases.

The low voltage energy supplementing module 80 works as an adjunct to the high voltage generator module 79 and generates supplementary defibrillation energy that is injected into the inputs of the pulse capacitor 81. The low voltage energy supplementing module 80 is electrically connected to the pulse capacitor 81 in line with the high voltage generator circuit 79 and is constructed using one or more low voltage ultra-capacitors that store supplemental defibrillation energy. By virtue of having the low voltage energy supplementing module 80 effectively "on tap" to augment the defibrillation energy, the load on the pulse capacitor 81 is thereby lower when compared to the load required to charge a pulse capacitor in a conventional AED, which, in turn, enables the high voltage generator module 79 and pulse capacitor 81 as used herein to be implemented with lower energy components. Furthermore, such lower energy components are well suited for use in an AED that is intended to be disposable and single use, where only a relatively reasonable degree of robustness is needed and reusability is not required. In addition, these components lower the cost, size and weight of the AED, enabling the AED to be packaged in a form factor that can readily fit into an average-sized pocket in a fashion analogous to contemporary mobile telephones.

The MCU 71 monitors the defibrillation waveform through the sensing circuit 87 and adjusts the supplemental defibrillation energy stored by switching the low voltage ultra-capacitors. A high voltage transformer is used by the low voltage energy supplementing module 79 to inject the stored supplemental defibrillation energy into the inputs of the pulse capacitor 81. This type of transformer can be packaged in a flat and thin planar design, known as a Planar Laminated High Energy Pulse Transformer, which is optimal for energy conversion efficiency and an ideal shape for a smartphone-like design. The low voltage energy supplementing module 80 uses a set of ultra-capacitors (or possible a single ultra-capacitor) in the range of 2.5V-48V and stores an amount of energy needed or to supplement a defibrillation pulse. The amount of supplementation varies depending on the application and target parameters of the device. The energy stored on the low voltage circuit could be as low as 10 J, or as high as 3 times the full defibrillation energy. The low voltage energy supplementing module 80 additively contributes to the energy generated by the high voltage generator module 79.

Figure 3:
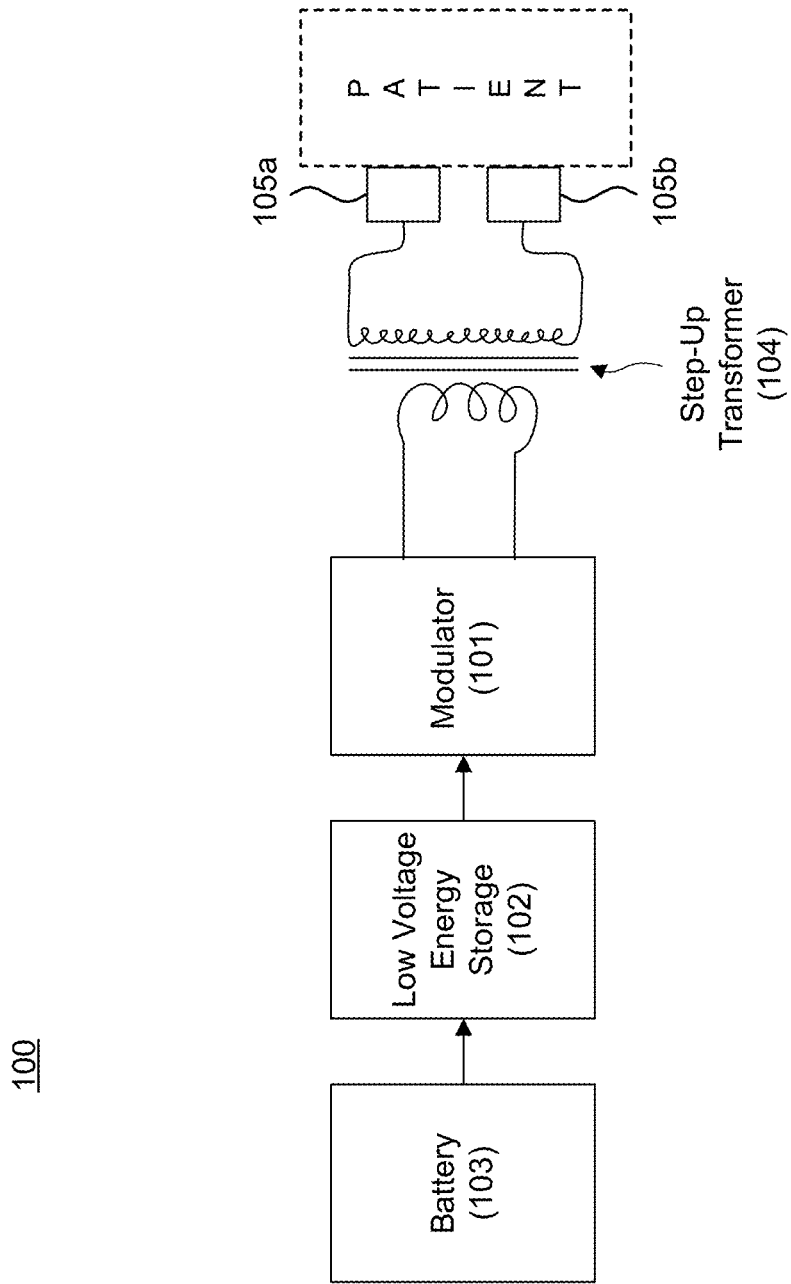
FIG. 3 is a schematic diagram showing a low voltage energy storage circuit for generating defibrillation waveforms energy in accordance with a further embodiment.

Low voltage energy storage for generating or supplementing defibrillation waveforms can be achieved through several circuits, as discussed with reference to FIGS. 3-7. While described in the context of use in personal AEDs, these low voltage high-energy storage circuits are adaptable for use in hospital defibrillators and in medic vehicle defibrillators as well as in implantable defibrillators. In its simplest form, energy is stored at a low voltage and switched through a step-up pulse transformer to generate the necessary defibrillation waveform, such as the biphasic waveform 181 (shown in FIG. 8). FIG. 3 is a schematic diagram showing a low voltage energy storage circuit 100 for generating defibrillation energy waveforms in accordance with one embodiment. Except as otherwise noted, the sensing and ECG circuits are omitted for clarity.

Here, the defibrillation circuit 100 includes four basic components, a pulse optimized step-up transformer 104 that feeds the defibrillation energy to a pair of electrodes 105*a-b*. The transformer 104 is driven by a modulator (or load switch) 101 that is fed by a low voltage energy storage module 102 containing one or more low voltage ultra-capacitors. Power is supplied by a battery 103. This circuit is completely open loop and relies upon pre-computed timing control pulses to instantiate an approximation to a defibrillation waveform. In addition, this circuit is simple and therefore low cost.

Figure 4:
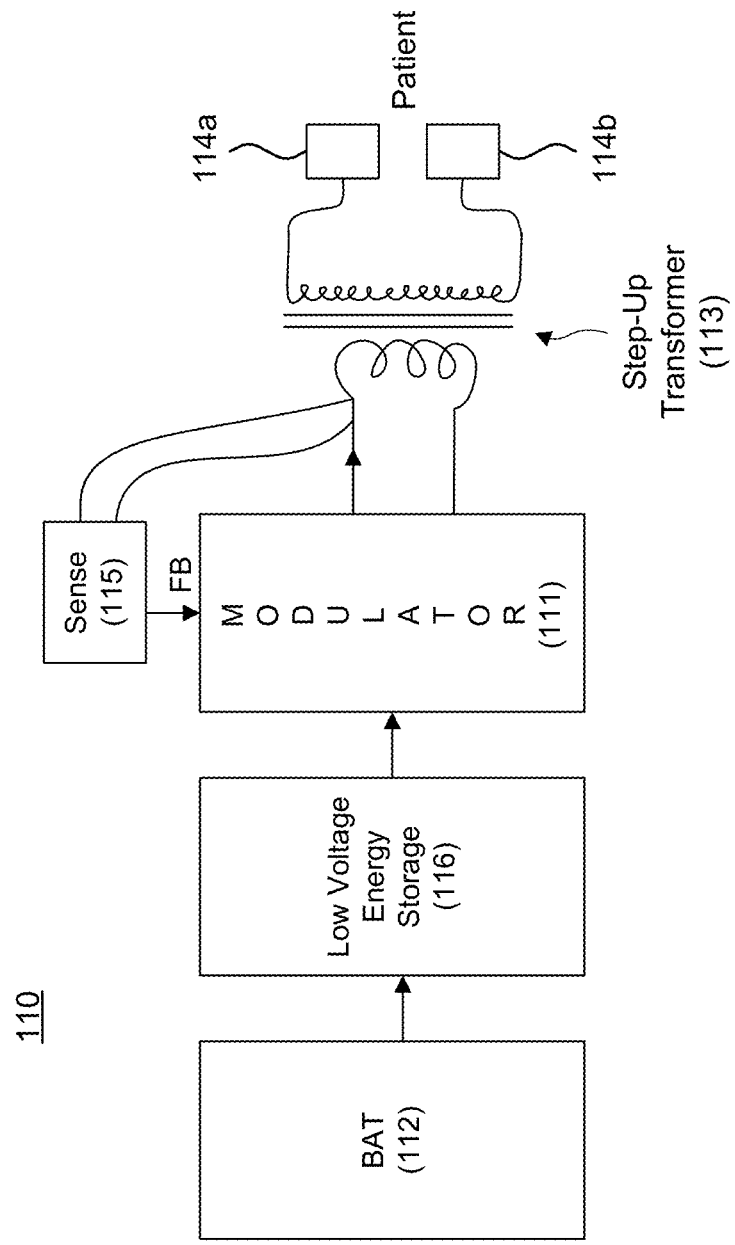
FIG. 4 is a schematic diagram showing a low voltage energy storage circuit for generating defibrillation waveforms energy with feedback in accordance with a further embodiment.

In another embodiment the electrical stimulus delivered to the patient can be monitored and inferred through current sensing employed on the primary side of the high-voltage pulse transformer. FIG. 4 is a schematic diagram showing a low voltage energy storage circuit 110 for generating defibrillation energy waveforms with feedback in accordance with a further embodiment. As before, the sensing and ECG circuits are omitted for clarity except as otherwise noted.

Here, the defibrillation circuit 110 includes four basic components, a pulse optimized step-up transformer 113, which serves to convert low-voltage high current energy to a high-voltage defibrillation pulse. A switch or modulator (or load switch) (111) to excite the high voltage pulse transformer that feeds the defibrillation energy to a pair of electrodes 114*a-b*. The transformer 113 is also driven by low voltage energy storage module 116 that generates supplementary energy through a bank of ultra-capacitors that are fed to the inputs of the transformer 113. Power is supplied by a battery 112. Additionally, a sensing module 115 includes sensing leads through which to monitor the inputs of the transformer 113, which is used by the sensing module 115 as feedback for switching the bank of ultra-capacitors, as required. The feedback is fed into a modulator (or load switch) 111 that controls the stimulus to the high voltage pulse transformer 113, which results in better control and regulation of the energy delivered to the patient regardless of patient impedance.

Figure 5:
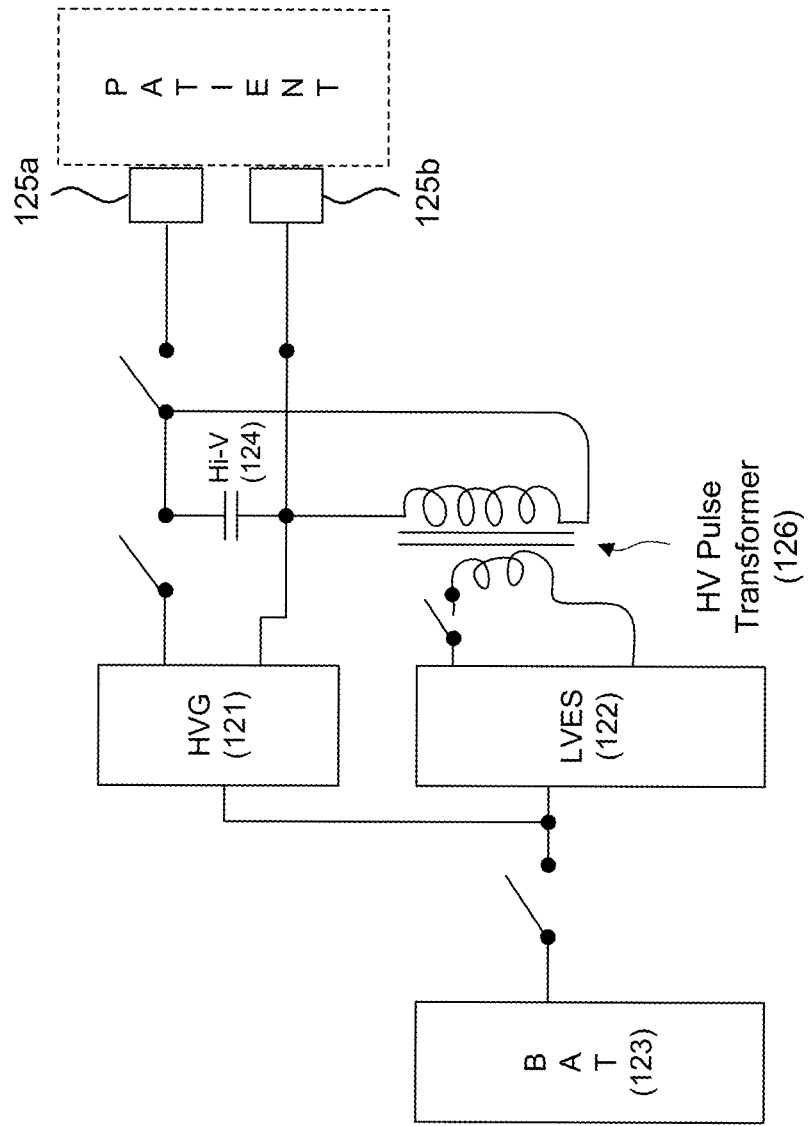
FIG. 5 is a schematic diagram showing a hybrid low voltage energy storage circuit for generating defibrillation waveforms energy in accordance with a further embodiment.

A hybrid energy sourcing approach can be taken by pre-charging a high-voltage capacitor in addition to a low-voltage pulse capacitor (or ultra-capacitor with pulse discharge capabilities). FIG. 5 is a schematic diagram showing a hybrid low voltage energy storage circuit 120 for generating defibrillation energy waveforms in accordance with a further embodiment. As before, the sensing and ECG circuits are omitted for clarity except as otherwise noted.

The defibrillation circuit 120 includes three basic components, a high voltage generator (HVG) circuit 121, which serves the purpose to charge a high voltage capacitor 124 that feeds the defibrillation energy to a pair of electrodes 125*a-b*. The high voltage generator boost circuit 121 is supplemented by a low voltage energy storage (LVES) circuit 122 coupled through a high voltage pulse transformer 126 that generates supplementary energy that is fed to the electrodes 125*a-b*. Power is supplied by a battery 123 through a switch. During discharge, some energy is supplied by the high voltage capacitor 124 while additional energy is discharged into the patient from the LVES circuit 122 through the high voltage pulse transformer 126. As the defibrillation energy is supplied by multiple sources, tradeoffs can be made between magnetic pulse transformer size and capacitor size, optimizing for the best available technology at the time. In this implementation, there is no control and feedback in the defibrillation pulse, which is a trade-off favoring simplicity and clinically reasonable efficacy versus complexity in favor of the appearance of perfection.

Figure 6:
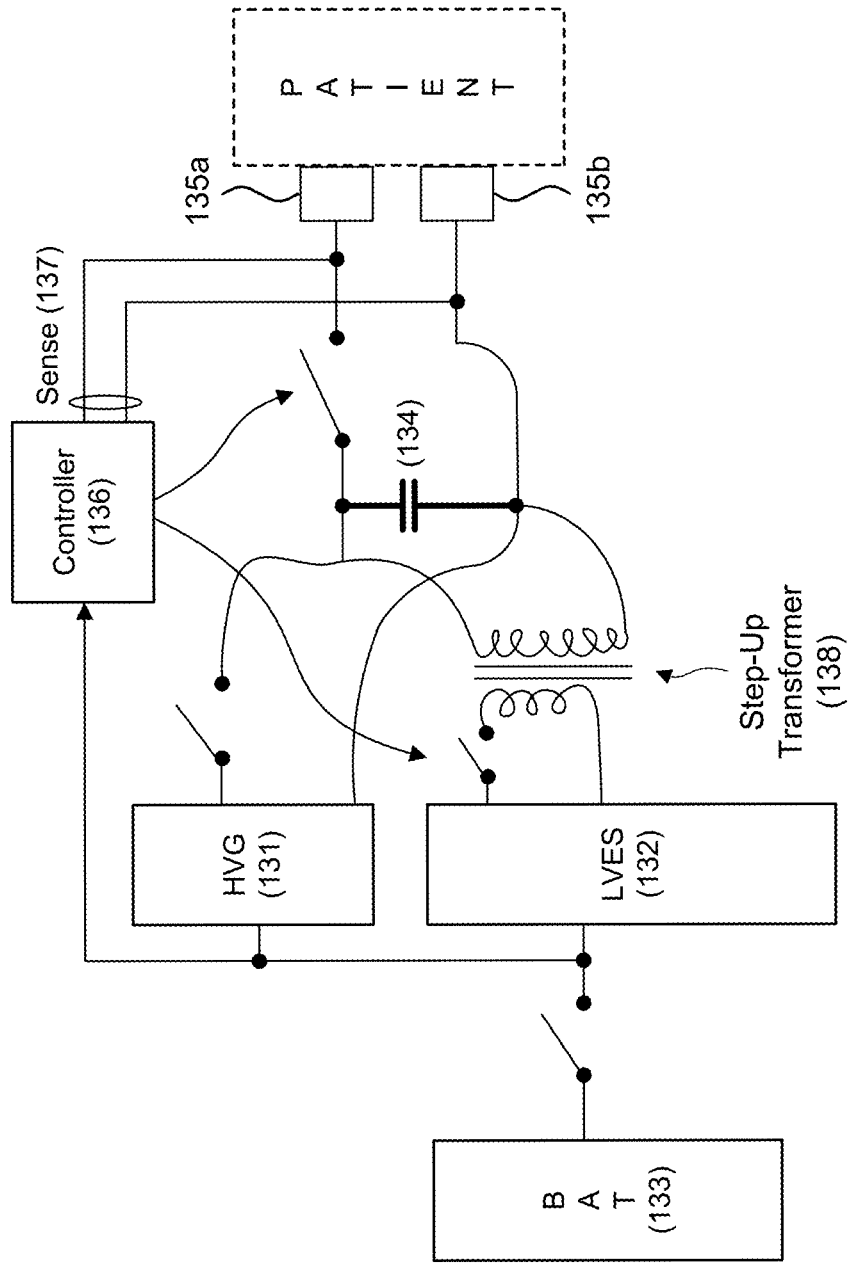
FIG. 6 is a schematic diagram showing a hybrid low voltage energy storage circuit for generating defibrillation waveforms energy with feedback in accordance with a further embodiment.

The foregoing hybrid energy delivery approach can be expanded upon with a controller that senses the therapy being delivered to the patient which allows active control and optimization of the defibrillation waveform depending on realtime impedance feedback. FIG. 6 is a schematic diagram showing a hybrid low voltage energy storage circuit 130 for generating defibrillation waveforms energy with feedback in accordance with a further embodiment. As before, the sensing and ECG circuits are omitted for clarity except as otherwise noted.

Here, the defibrillation circuit 130 includes four basic components, a high voltage generator (HVG) circuit 131, which similarly serves to charge a high voltage capacitor 134 that feeds the defibrillation energy to a pair of electrodes 135*a-b* when defibrillating. The low voltage energy storage (LVES) circuit 132 is supplemented by a bank of ultra-capacitors connected through a step-up pulse transformer 138 that generates supplementary energy that is fed to the inputs of the H-bridge. Power to the system is supplied by a battery 133. Additionally, a controller 136 includes sensing leads 137 through which to monitor the patient and the energy delivered. This waveform is used by the controller 136 as feedback for switching the bank of ultra-capacitors on and off to deliver supplementary energy as required. The controller 136 can modify the amount of energy being transferred to the patient in real time by shutting off or activating the low voltage storage element delivering additional energy to the patient only when needed resulting in a more accurate and efficacious defibrillation waveform. Long-duration defibrillation pulses, that is, a waveform with a duration greater than 20 milliseconds (msec), can be counter-productive, as can occur in select patients with high resistance and impedance to current delivery. Contrarily, ultra-low resistance patients, such as small children, can manifest too brief of a defibrillation waveform, that is, a waveform with a duration of less than 4 msec, perhaps also impeding defibrillation efficiency.

Figure 7:
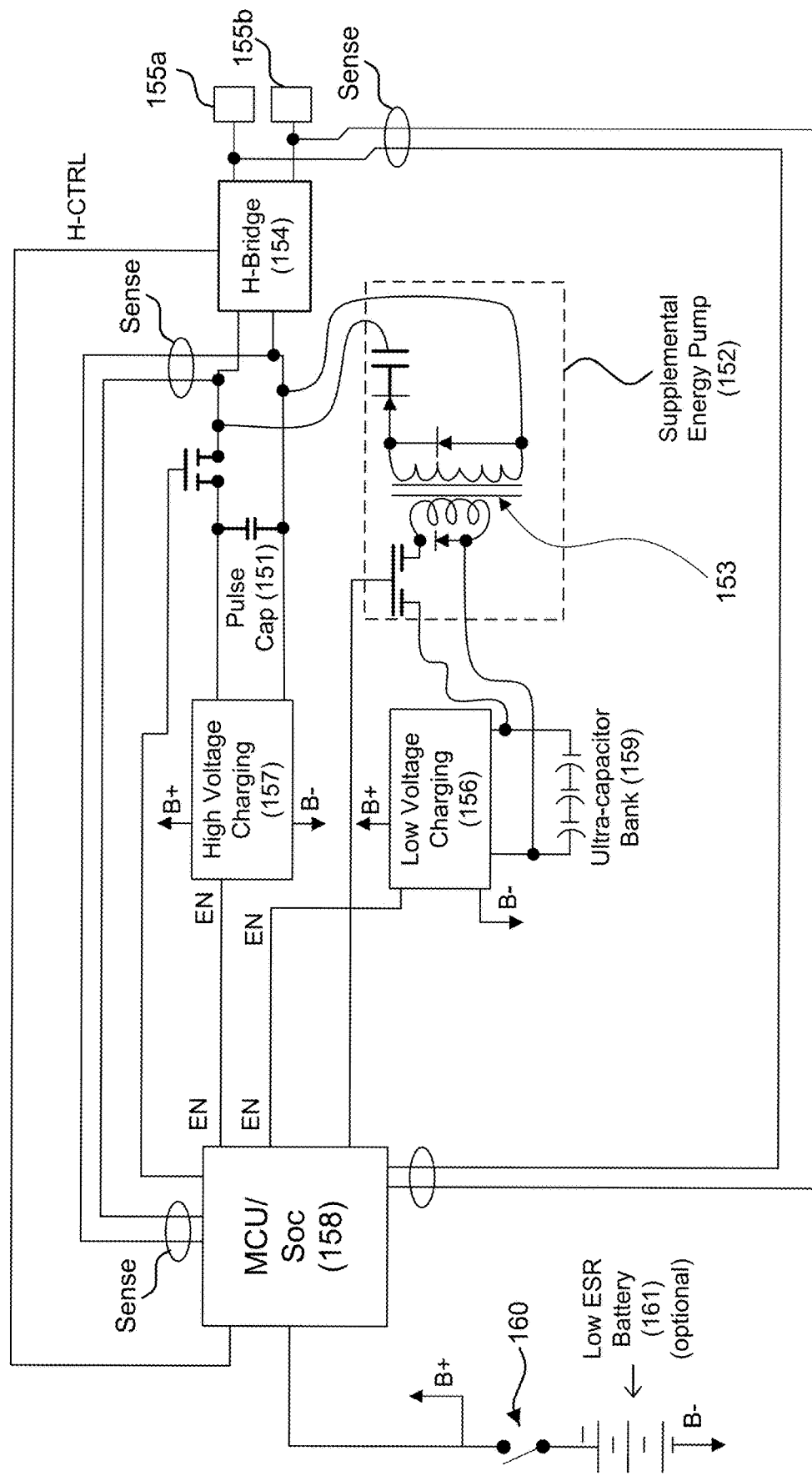
FIG. 7 is a schematic diagram showing a hybrid low voltage energy storage circuit for generating defibrillation waveforms energy with feedback and supplemental energy pump in accordance with a further embodiment.

The foregoing hybrid energy delivery approach with feedback can be improved upon with the addition of a supplemental energy pump. FIG. 7 is a schematic diagram showing a hybrid low voltage energy storage circuit 150 for generating defibrillation waveforms energy with feedback and supplemental energy pump 152 in accordance with a further embodiment. The circuit 150 is controlled by a microcontroller (MCU) or system-on-chip (SOC) 158 (hereafter, simply "MCU").

The supplemental energy pump 152 is able to dynamically couple energy stored in an optional low voltage charging module 156 into the patient through a transformer 153 incorporated into the supplemental energy pump 152 with high voltage stored in a high voltage charging module 157. This approach provides superior control of the energy delivery and waveform. The pumping action decreases the dielectric withstand voltage requirements and step-up transformer sizing requirements required by the hybrid low voltage energy storage circuit 150; thus, the respective breakdown voltage and voltage increase can be significantly lower here when compared to a conventional AED intended for long term reusability, that is, non-disposable multiple victim use. In turn, lower voltage and capacitance components can be safely used throughout the hybrid low voltage energy storage circuit 150, including a lower capacity power source. Moreover, given the dynamic nature of the circuit, the circuit 150 is capable of high efficacy on a wide variety of patients and allows additional flexibility for the internal components to be selected to optimize for cost, size, and weight. This approach also features an optional H-bridge 154 coupled output to further simplify the generation of a biphasic pulse or correct for incorrect (reversed) placement of the electrodes 155a-b.

As with conventional AEDs, defibrillation energy is stored in a pulse capacitor 151. A high voltage charging module 157 conventionally increases voltage drawn from a battery 161 with a low equivalent series resistance (ESR) rating, drawn through a rectification circuit (not shown) to convert the energy into DC, which is then stored in the pulse capacitor 151. However, the low voltage charging module 156 is coupled to a bank of ultra-capacitors 159, which only need to be rated to handle modest low voltages in the range of 2.5V-48V with a capacitance range yielding up to 360 J, which would be in the range of 96 Farads (F) for 2.5V and 0.26 F for a voltage of 48V. The bank of ultra-capacitors 159 is preferably arranged in series, series-parallel or parallel configurations to store up to 360 J of energy or more.

The supplemental energy pump 152 is enabled by the MCU 158 when the H-bridge 154, if present, is discharging energy into the patient to maintain the defibrillation shock for several milliseconds; the bank of ultra-capacitors 159 have a high discharge rate that allows the low voltage charging module 156 to additively augment the defibrillation energy during shock delivery. The supplemental energy pump 152 allows the pulse energy to be stepped up during delivery by interfacing with the H-bridge's input leads. The MCU 158 can monitor the supplementing energy being delivered by the low voltage charging module 156 over a pair of sensing connections that interface with the H-bridge's output leads.

With this form of energy supplementation, a lower rated high-voltage pulse capacitor 151 can be used than found in conventional AEDs, and, given the expected disposable single use operation of an AED using the hybrid low voltage energy storage circuit 150, the circuit 150 can be powered using a low cost and lightweight battery 156, rated in the range of 2.5V-48V. In turn, the use of such a small form factor battery allows an AED using the hybrid low voltage energy storage circuit 150, such as discussed with reference to FIGS. 10-18, to be both disposable and carriable in an average pocket. In a further embodiment, the battery 161 is supplemented with a manual switch 160 to create an open circuit when not in use, which conserves battery and component life and simplifies the design. In a still further embodiment, an AED using the hybrid low voltage energy storage circuit 150 includes a battery charging circuit (not shown) with which to recharge the battery 161. A similar component rating reduction of the pulse capacitor circuit would be applicable where the foregoing circuits are adapted for use in a non-portable clinical-grade defibrillator and in an implantable defibrillator, the latter of which could also benefit from a battery supply rating reduction.

Figure 8:
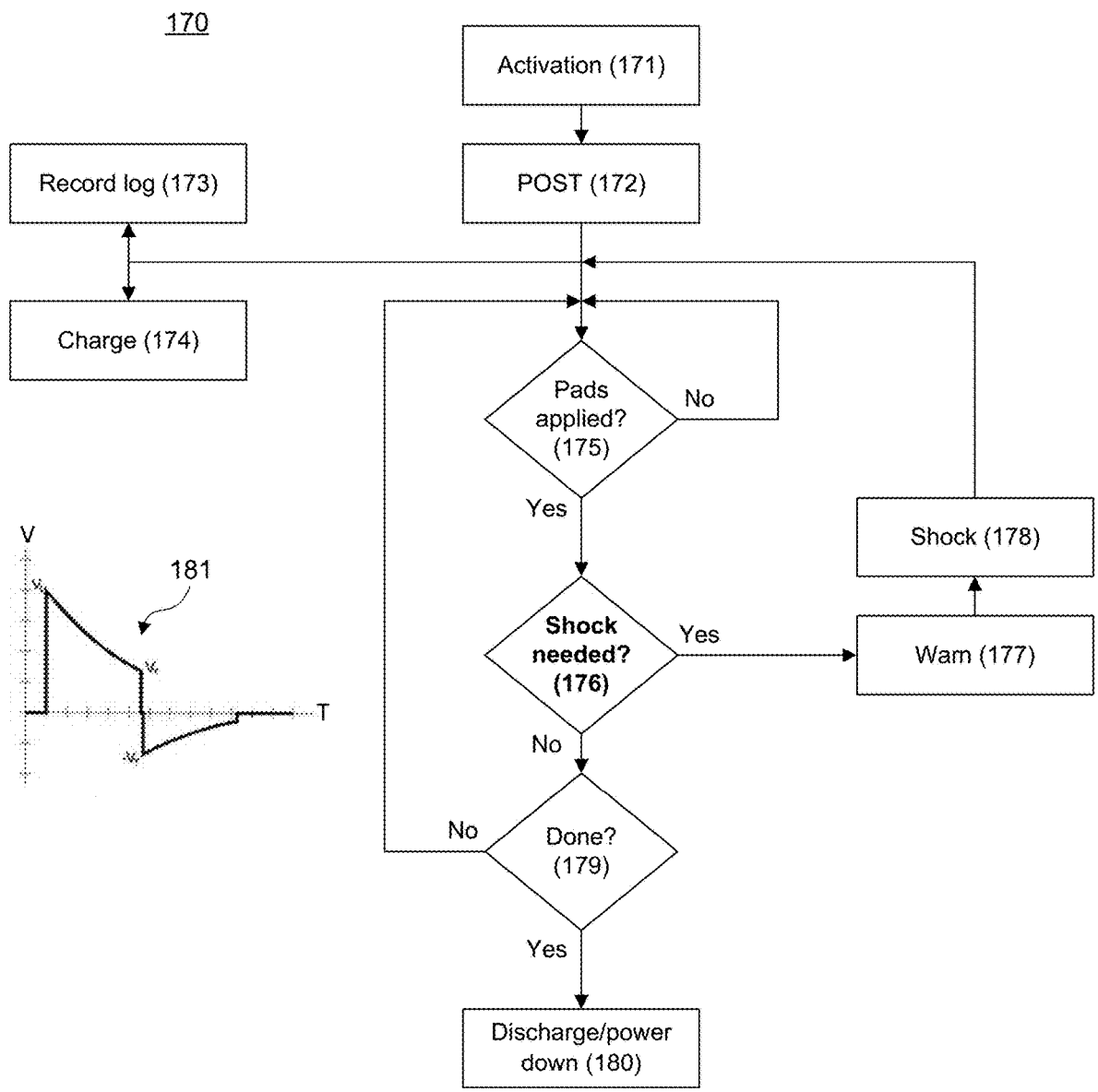
FIG. 8 is a flow chart showing a method for operating a disposable single use pocketable AED in accordance with one embodiment.

A disposable pocketable AED using the hybrid low voltage energy storage circuit 150 is intended to be available 24/7/365 and easy to use with little to no training required. FIG. 8 is a flow chart showing a method 170 for operating a disposable pocketable AED in accordance with one embodiment. To start, the AED is activated (step 171) by the user pressing the "On" switch, or similar control, after which the AED executes a power-on self-test (POST) (step 172).

Figure 9:
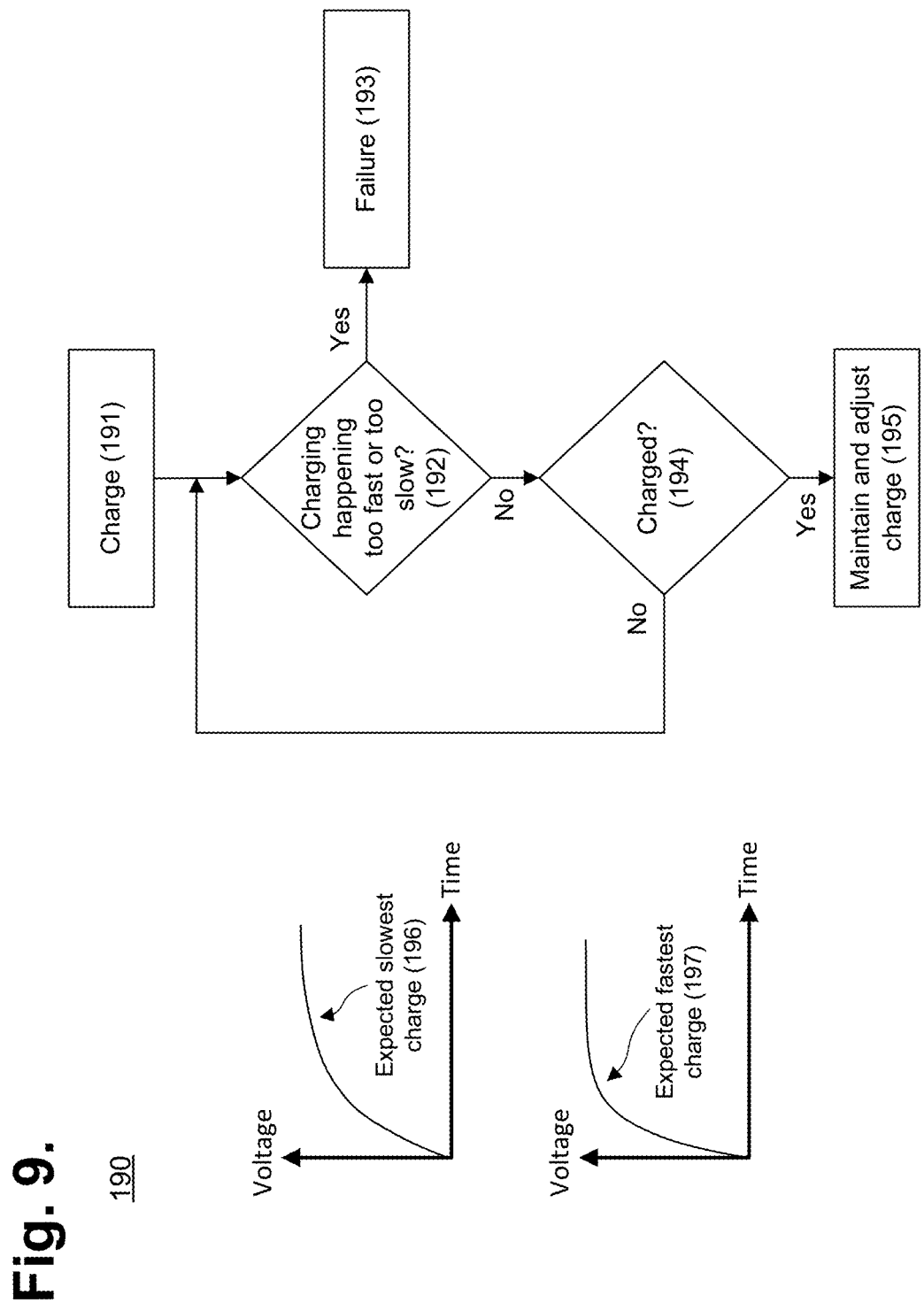
FIG. 9 is a flow chart showing a charging routine for use in the method of FIG. 8.

Following successful POST (step 172), both a record of the AED's activation is made in an onboard log (step 173) and the pulse capacitor is pre-charged to a conservative level (step 174) by a combination of the high voltage charger module and the low voltage energy storage circuit, as further described below with reference to FIG. 9. The state of the electrode pads is determined and the methodology only proceeds once the pads are correctly applied (step 175). The AED determines whether a shockable rhythm is present (step 176).

Provided a shockable rhythm is sensed (step 176), the AED issues a warning to the user (step 177) and a defibrillation shock is delivered (step 178). The defibrillation shock is delivered as a high voltage therapeutic waveform 181, preferably as a biphasic waveform, such as a biphasic truncated exponential (BTE), pulsed biphasic, and rectilinear biphasic waveform, modified biphasic, arbitrary or, alternatively, as a monophasic waveform. Other defibrillation waveforms are possible. Once the shock has been delivered, the device determines whether a normal rhythm has been restored and, if so, the methodology is done (step 179) and the AED will discharge the pulse capacitor and power down (step 180) after 15 minutes of a non-VF rhythm. In some cases, several defibrillation shocks are required and the AED delivers biphasic defibrillation shocks, where the initial energy level for defibrillation begins at 120 J and either repeats or escalates for the second and subsequent defibrillation shocks up to a maximum of 360 J. In the use of escalation, the defibrillation energy is automatically adjusted by the AED with each subsequent defibrillation shock. In a further embodiment, the polarity of the defibrillation shock is reversed on the third shock (or any subsequent shock following the first shock) should no restoration of a non-shockable rhythm occur. In a further embodiment, the AED can automatically limit the number of shock re-attempts permitted, as after three defibrillation shocks, resuscitation of the victim 18 becomes unlikely.

In a further embodiment, as part of the process of delivering the defibrillation shock (step 178), the AED measures patient impedance during application of the defibrillation shock through the sensing circuit and adjusts one or more of the energy, voltage, and pulse width of the defibrillation waveform 181 in real time to generate optimal defibrillation therapy, where the x-axis represents time (T) and the y-axis represents voltage (V). Knowledge of patient impedance is crucial in a traditional design, which is used to determine the energy required to pre-charge the high-voltage pulse capacitor to an appropriate level and to aid in realizing an appropriate energy deliver waveform. In practice, patient impedance changes during the shock, so conventional impedance-based pre-charge circuits have limited usefulness in achieving effective defibrillation. For instance, the impedance of a ten-year-old child is around 20 Ohms, whereas a 200-pound, middle-aged male has an impedance of about 75 Ohms. For both individuals, a waveform of 10 msec is likely necessary for effective defibrillation but their defibrillation energy and pre-charge parameters are significantly different. Moreover, impedance on the skin's surface typically decreases as defibrillation therapy progresses. Thus, MCU 71 (shown in FIG. 2) interfaces to the sensing circuit to continually measure impedance in real time and adjusts parameters in the high voltage energy delivery module 79 and the low voltage energy supplementing module 80 to alter energy, voltage and pulse width (duration). Other parameters are possible.

For instance, an exemplary biphasic waveform is defined with an asymmetrical 65% tilt from a leading-edge voltage $V_L$ and trailing edge voltage $V_T/-V_T$ with a polarity reversal halfway through the waveform. Patient impedance can affect the duration of the waveform where increased impedance means longer pulse width, lower voltage, or less energy to the heart, and decreased impedance means shorter pulse width, higher voltage, or more energy to the heart (unless patient impedance changes after the impedance is sensed). The most efficacious way to ensure correct energy delivery is to monitor and adjust the therapy in real time. One or more of these parameters can be adjusted by the MCU in real time to alter the amount of primary or supplementary energy contour of the shock to reflect the ideal target therapy represented by the biphasic waveform.

The AED utilizes low voltage energy storage to supplement the defibrillation circuit's pulse capacitor. FIG. 9 is a flow chart showing a charging routine 190 for use in the method 170 of FIG. 8. The primary and supplementary defibrillation energy is based on a high voltage therapeutic waveform, such as the biphasic waveform shown in FIG. 8, which can be maintained by the microcontroller 71 (shown in FIG. 2) in its memory store. In a further embodiment, the AED measures patient impedance during application of the defibrillation shock and adjusts one or more of the energy, voltage, and pulse width of the defibrillation waveform 181 in real time to generate optimal defibrillation therapy and, in a still further embodiment, the AED can revise the optimal defibrillation therapy during the second and, if needed, third defibrillation pulses in the event that earlier defibrillation attempts have failed to restore normal cardiac rhythm. During charging of the pulse capacitor (step 191), the microcontroller compares the primary defibrillation energy and the supplemental energy to the energy required to deliver the defibrillation waveform 181. If the charging of the pulse capacitor is happening either too fast or too slow (step 192), as based on a plot of an expected slowest charging rate 196 and a plot of an expected fastest charging rate 197, a failure condition exists (step 193). The charging rate can be bounded, for instance, based on a pair of thresholds that respectively define upper and lower bounds of charging rate, such that a charging rate that exceeds the upper bound is considered too fast and a charging rate that falls below the lower bound is considered too slow. A failure condition in the expected charging rate can be useful in identifying potential problems with the charging circuit. An overly fast charging rate could indicate that capacity of pulse capacitor has decreased and may not have enough energy to perform its function when fully charged. An overly slow charging rate falling below the lower bound could indicate an excessive energy leakage in the circuit, which typically ends up being expressed as heat. In both charging rate plots, the x-axes represent time and the y-axes represent voltage. Otherwise, charging continues until the circuit is charged (step 194), after which the microcontroller maintains and adjusts the charge in the pulse capacitor as needed (step 195).

Figure 10:
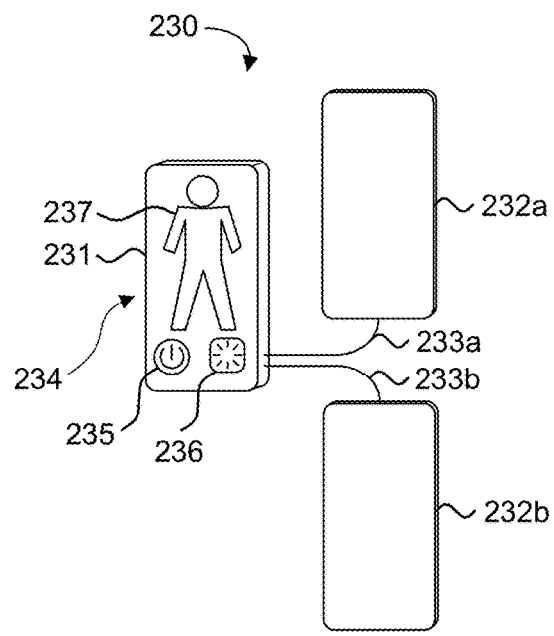
FIG. 10 is a front view showing a disposable single use pocketable AED with dual free-floating electrodes in accordance with one embodiment.

FIG. 10 is a front view showing a disposable single use pocketable AED with dual free-floating electrodes in accordance with one embodiment. The AED 230 combines a highly portable form factor with high and low voltage energy storage circuits that deliver defibrillating energy out of only modest lightweight battery capacity. Such a pocket-sized AED can be made readily available not just in the home, but anytime and anywhere that a would-be rescuer happens to be. The AED 230 advantageously uses low voltage energy storage, as discussed supra with reference to FIG. 2 et seq., to supplement the high voltage charger circuit used to charge the pulse capacitor. This innovation allows the circuit to be powered with a low cost and lightweight battery and the high voltage charger circuit and pulse capacitor to be down-rated from the high capacitance levels utilized in conventional designs, all of which significantly decreases cost and size, thereby making single-use and device disposability possible.

The AED 230 is housed in a small lightweight housing 231, about the size and weight of a mobile telephone, that is, in the range of 2.25 to 3.5 inches wide, 5.25 to 7 inches tall, and 0.25 to 1.0 inches deep and a weight in the range of 130 to 550 grams. Other sizes and form factors are possible. The pair of free-floating electrodes 232*a-b* are connected to the housing 231 by a pair of flexible leads 233*a-b*. A planar laminated high energy pulse transformer is incorporated into each electrode 232*a-b*, as further discussed infra with reference to FIG. 19. Each electrode 232*a-b* is coated with an adhesive hydrogel that ensures proper contact with the victim's skin. The electrodes 232*a-b* are for a single-use only. The front of the AED 230 has a user interface 234 designed to optimize user understanding that includes a set of visual instructions 237. Optionally, the AED 230 can be equipped with a speaker (not shown) to generate voice prompts.

The AED 230 includes a streamlined and simple user interface that facilitates understanding and proper use during an emergency by lay people. Power is controlled by a simple "On" switch 235 and the status of the AED 230 is intuitively provided by a visual indicator 236 that changes color depending upon the state of the AED, for instance, through a display of "red," "yellow" and "green" to respectively indicate device activated but not attached to the patient, device attached and pulse capacitor charging, and a readyto-shock condition. Other colors, forms and types of indicators are possible. In a further embodiment, the AED 230 includes mobile communications capabilities by which to automatically summon medical assistance, generally by calling 9-1-1 or the equivalent in most localities, upon the sensing of a shockable rhythm. The mobile communications capabilities integrated into the AED 230 by including appropriate circuits and components or through a special features module providing the mobile communications capabilities to the AED. The AED could also receive mobile communications capabilities through a wireless interface, such as WiFi or Bluetooth, over which the AED can communicate to a mobile phone or wide area network, such as the Internet, and relay a 9-1-1 call. Alternatively, a mobile phone or device could be supplemented with the features of the AED 230.

Figure 11:
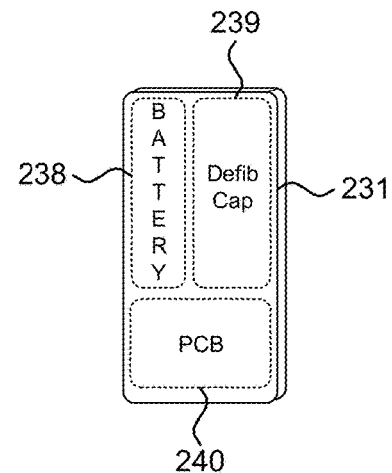
FIG. 11 is a cut-away view showing block component groups contained within the disposable single use pocketable AED of FIG. 10.

FIG. 11 is a cut-away view showing block component groups contained within the disposable single use pocketable AED 230 of FIG. 10. The AED's circuit is provided on a printed circuit board (PCB) 240 contained within the housing 231, which also contains a low-cost, high-energy density battery 238 (optionally, a primary cell) and a pulse capacitor 239.

Figure 12:
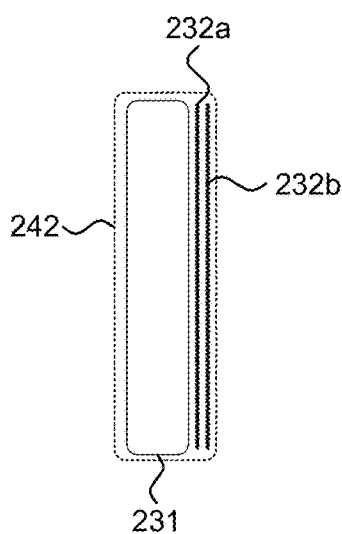
FIG. 12 is a side view showing the disposable single use pocketable AED of FIG. 10 with the housing and dual free-floating electrodes stowed in a carrying case.

FIG. 12 is a side view showing the disposable single use pocketable AED 230 of FIG. 10 with the housing and dual free-floating electrodes stowed in a carrying case 242. The AED 230 is intended to be easily carried in a pocket and could be carried in a purse, backpack, glovebox, golf bags, and so forth, so as to enable the AED 230 to be conveniently on-hand in case of an SCA situation in the same manner that most people have their mobile phone on-hand.

Figure 13:
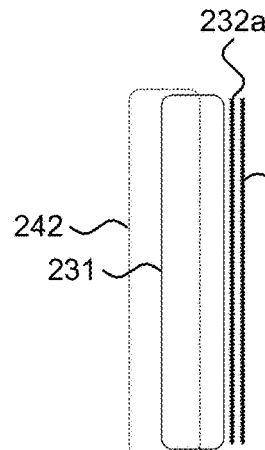
FIG. 13 is a side view showing the disposable single use pocketable AED of FIG. 10 with the housing and dual free-floating electrodes partially deployed from the carrying case.

FIG. 13 is a side view showing the disposable single use pocketable AED 230 of FIG. 10 with the housing and dual free-floating electrodes partially deployed from the carrying case 242. The pair of free-floating electrodes 232*a-b* share a similar front profile with the housing 231. The housing 231 and electrodes 232*a-b* slide out of the carrying case 242 when being deployed.

Figure 14:
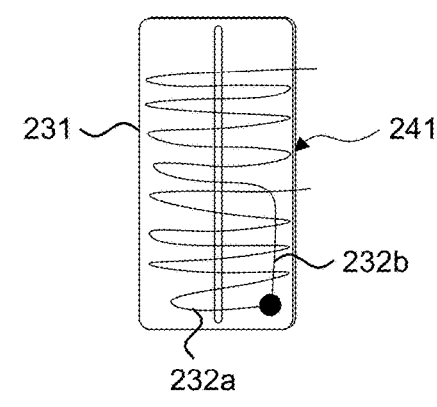
FIG. 14 is a back view showing the cable management system of the disposable single use pocketable AED of FIG. 10.

FIG. 14 is a back view showing the cable management system 241 of the disposable single use pocketable AED 230 of FIG. 10. A cable management system 241 is used to store the leads 232*a-b* inside of the housing 231, where the leads are internally retracted by the smart cable management system 241 until needed.

Figure 15:
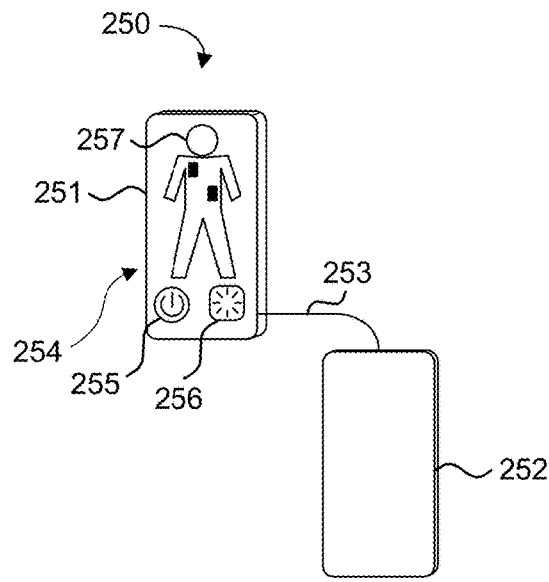
FIG. 15 is a front view showing a disposable single use pocketable AED with a single free-floating electrode in accordance with one embodiment.

One of the dual free-floating leads 232*a-b* can be eliminated by providing an electrode pad surface on the AED's housing. FIG. 15 is a front view showing a disposable single use pocketable AED 250 with a single free-floating electrode 252 in accordance with one embodiment. As before, the AED 250 is housed in a small lightweight housing 251, but only one free-floating electrode 252 is connected to the housing 31 by a single flexible lead 25.

Figure 16:
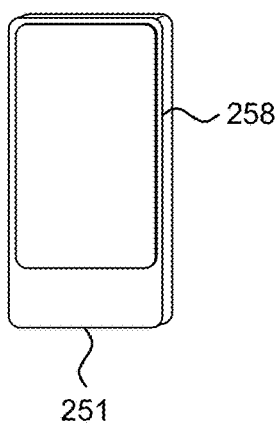
FIG. 16 is a rear view showing the integrated electrode of the disposable single use pocketable AED of FIG. 15.

FIG. 16 is a rear view showing the integrated electrode 258 of the disposable single use pocketable AED 250 of FIG. 15. An integrated electrode pad 258 is provided on a rear-facing surface of the housing 251. A planar laminated high energy pulse transformer is incorporated into each electrode 252, 258, as further discussed infra with reference to FIG. 19. Both the single free-floating electrode 252 and integrated electrode 258 are coated with an adhesive conductive hydrogel that ensures proper contact with the victim's skin. The front of the AED 250 similarly has a user interface 254 designed to optimize user understanding that includes a set of visual instructions 257. Optionally, the AED 250 can be equipped with a speaker (not shown) to generate voice prompts. Power is again controlled by an "On" switch or optionally an activation circuit 255 and the status of the AED 250 is provided by a visual indicator 256. The AED's circuit is provided on a PCB (not shown) contained within the housing 251, which also contains a low-cost, high-energy density battery (not shown) and pulse capacitor (not shown).

Figure 17:
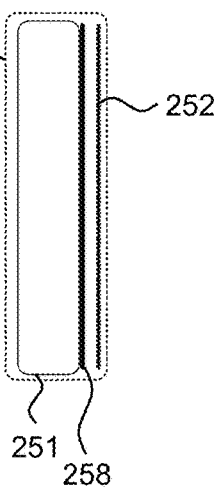
FIG. 17 is a side view showing the disposable single use pocketable AED of FIG. 10 with the housing and single free-floating electrode stowed in a carrying case.

FIG. 17 is a side view showing the disposable single use pocketable AED 250 of FIG. 10 with the housing 251 and single free-floating electrode 252 stowed in a carrying case. The single free-floating electrode 252 shares a similar profile with the housing 251.

Figure 18:
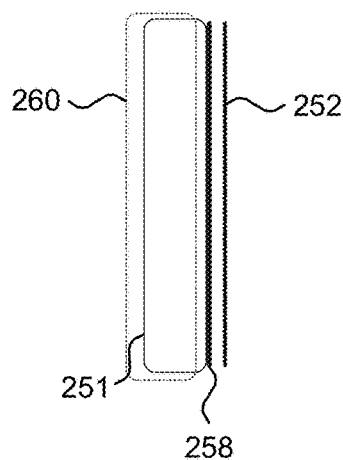
FIG. 18 is a side view showing the disposable single use pocketable AED of FIG. 10 with the housing and single free-floating electrodes partially deployed from the carrying case.

FIG. 18 is a side view showing the disposable single use pocketable AED of FIG. 10 with the housing and single free-floating electrodes partially deployed from the carrying case. The housing 251 and electrode 252 slide out of the carrying case 260 when being deployed. A smart cable management system (not shown) is also used to store the single lead 253 inside of the housing 251, where the lead is internally retracted by a cable management system until needed.

Figure 19:
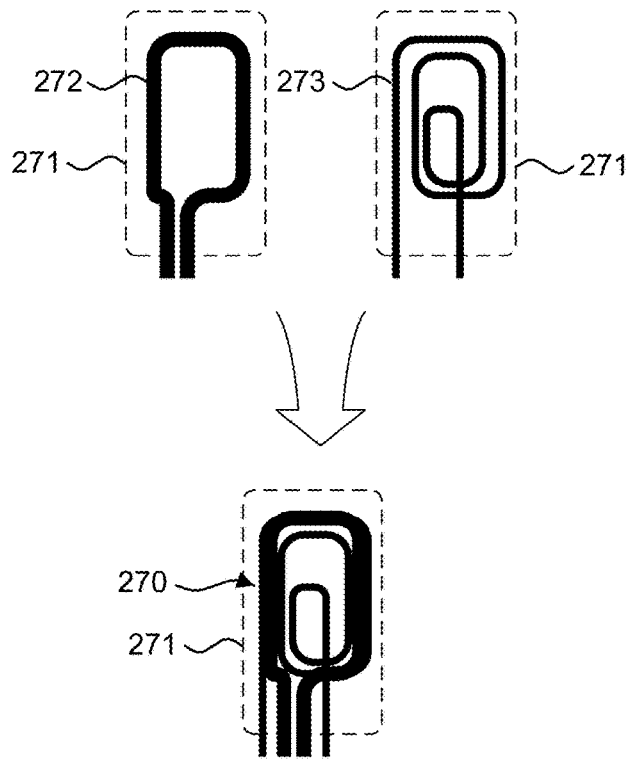
FIG. 19 is a top view diagram showing an electrode pad assembly for use in the disposable single use pocketable AEDs of FIGS. 10 and 15.

FIG. 19 is a top view diagram showing an electrode pad assembly 271 for use in the disposable single use pocketable AEDs 230, 250 of FIGS. 10 and 15. Each electrode contains an embedded planar laminated high energy pulse transformer. This type of transformer exhibits high power density by functioning at high switching frequencies, while packaged in a low profile with larger surface area, thereby preventing overheating. In each electrode assembly 271, a primary winding 272 and a secondary winding 273 are laminated together into a planar transformer 270 with a jumper that is soldered, welded, crimped, or otherwise electrically conducted together.

The circuit described herein provides for the delivery of a high voltage, high energy pulse for use in external defibrillation through a design that decreases overall device cost, size and weight by meaningfully innovating alternatives to capacitor charging through the use of low voltage, high current supplementary defibrillation energy storage and delivery. The circuit enables high energy densities with low cost, weight and size.

In addition, the circuit provides the basis for external defibrillators that are easy to carry, low cost and lightweight, while delivering a high-voltage, high-energy biphasic shock suitable for cardiac defibrillation and victim resuscitation. External defibrillators utilizing this circuit can help to facilitate the widespread adoption of the portable defibrillation technology and thereby meaningfully help to decrease the number of deaths from sudden cardiac arrest. Moreover, such circuits could also aid in reducing size and cost of implantable defibrillators.

While the invention has been particularly shown and described as referenced to the embodiments thereof, those skilled in the art will understand that the foregoing and other changes in form and detail may be made therein without departing from the spirit and scope of the invention.

What is claimed is:

1. A circuit for use in generating a defibrillation waveform, comprising:
   a low voltage energy storage module comprising one or more low voltage ultra-capacitors that store low voltage energy;
   a pair of electrodes;
   a pulse transformer incorporated into each of the electrodes to convert the low voltage energy to high voltage defibrillation energy and to provide the defibrillation energy to the electrodes configured to be applied to a patient;

a modulator to receive the low voltage energy from the low voltage energy storage module and transfer the low voltage energy to the pulse transformer; and
a battery.

2. A circuit in accordance with claim 1, further comprising:
a sensing circuit configured to sense a shockable cardiac rhythm that constitutes a cardiac arrest condition in the patient.

3. A circuit in accordance with claim 2, further comprising:
sensing leads comprised in the sensing circuit and configured to monitor inputs of the pulse transformer.

4. A circuit in accordance with claim 3, wherein the ultra-capacitors are switched based on the inputs of the pulse transformer.

5. A circuit in accordance with claim 3, wherein the modulator controls the transfer of the low voltage energy to the pulse transformer based on the inputs of the pulse transformer.

6. A compact external defibrillator for use in generating a defibrillation waveform, comprising:
a case;
a circuit enclosed in the case, comprising:
a low voltage energy storage module comprising one or more low voltage ultra-capacitors that store low voltage energy; and
a pulse transformer incorporated into each of a pair of electrodes and configured to convert the low voltage energy to high voltage defibrillation energy; and
the pair of electrodes, each configured to deliver the defibrillation energy to the patient, wherein three sides of the housing are directly adjacent to at least one of the electrodes when placed in the case.

7. A compact external defibrillator in accordance with claim 6, further comprising:
a modulator to receive the low voltage energy from the low voltage energy storage module and transfer the low voltage energy to the pulse transformer.

8. A compact external defibrillator in accordance with claim 6, further comprising:
a sensing circuit adapted to sense a shockable cardiac rhythm that constitutes a cardiac arrest condition in the patient.

9. A compact external defibrillator in accordance with claim 8, further comprising:
sensing leads comprised in the sensing circuit and configured to monitor inputs of the pulse transformer.

10. A compact external defibrillator in accordance with claim 9, wherein the ultra-capacitors are switched based on the inputs of the pulse transformer.

11. A compact defibrillator according to claim 9, wherein the modulator controls the transfer of the low voltage energy to the pulse transformer based on the inputs of the pulse transformer.

12. A compact defibrillator according to claim 6, wherein the housing comprises dimensions in the range of 2.25 to 3.5 inches wide, 5.25 to 7 inches tall, and 0.25 to 1.0 inches deep.

13. A single use external defibrillator, comprising:
a housing;
a circuit enclosed in the housing, comprising:
a low voltage energy storage module comprising one or more low voltage ultra-capacitors that store low voltage energy; and
a pulse transformer incorporated into each of a pair of electrodes and configured to convert the low voltage energy to high voltage defibrillation energy; and
the pair of electrodes through which the defibrillation energy is provided to a patient, wherein the housing and pair of electrodes are disposed of after the defibrillation energy is provided to the patient.

14. A single use external defibrillator in accordance with claim 13, further comprising:
a sensing circuit adapted to sense a shockable cardiac rhythm that constitutes a cardiac arrest condition in the patient.

15. A single use external defibrillator in accordance with claim 14, further comprising:
sensing leads comprised in the sensing circuit and configured to monitor inputs of the pulse transformer.

16. A single use external defibrillator in accordance with claim 15, wherein the ultra-capacitors are switched based on the inputs of the pulse transformer.

17. A single use external defibrillator in accordance with claim 15, wherein a modulator controls the transfer of the low voltage energy to the pulse transformer based on the inputs of the pulse transformer.

18. A single use external defibrillator in accordance with claim 13, further comprising at least one of:
a battery to power the circuit.

19. A single use external defibrillator in accordance with claim 13, further comprising:
a user interface provided on a surface of the housing.

20. A single use external defibrillator in accordance with claim 13, wherein the housing comprises dimensions in the range of 2.25 to 3.5 inches wide, 5.25 to 7 inches tall, and 0.25 to 1.0 inches deep and a weight in the range of 130 to 550 grams.

* * * * *